(12) United States Patent  
Kligerman et al.

(10) Patent No.: US 9,358,242 B2  
(45) Date of Patent: Jun. 7, 2016

(54) CALCIUM GLYCEROPHOSPHATE FOR TREATING AND PREVENTING RESPIRATORY DISEASES OR CONDITIONS

(75) Inventors: Alan E. Kligerman, Egg Harbor Township, NJ (US); Margaret T. Weis, Amarillo, TX (US)

(73) Assignee: Prelief Inc., Egg Harbor Township, NJ (US)

( * ) Notice: Subject to any disclaimer, the term of this patent is extended or adjusted under 35 U.S.C. 154(b) by 800 days.

(21) Appl. No.: 12/714,700

(22) Filed: Mar. 1, 2010

(65) Prior Publication Data

US 2010/0158819 A1      Jun. 24, 2010

Related U.S. Application Data

(63) Continuation-in-part of application No. PCT/US2008/074589, filed on Aug. 28, 2008.

(60) Provisional application No. 60/968,938, filed on Aug. 30, 2007, provisional application No. 61/285,260, filed on Dec. 10, 2009.

(51) Int. Cl.
*A61K 31/66* (2006.01)
*A61K 9/00* (2006.01)
*A61M 15/00* (2006.01)

(52) U.S. Cl.
CPC ............... *A61K 31/66* (2013.01); *A61K 9/0043* (2013.01); *A61M 15/009* (2013.01)

(58) Field of Classification Search
None
See application file for complete search history.

(56) References Cited

U.S. PATENT DOCUMENTS 4,885,287 A * 12/1989 Hussain et al. ............... 514/159
5,419,898 A *  5/1995 Ikejiri et al. ............... 424/78.04

(Continued)

OTHER PUBLICATIONS

International Search Report and Written Opinion for the related International Application No. PCT/US08/74589 issued on Nov. 18, 2008.

(Continued)

*Primary Examiner* — Carlos Azpuru
*Assistant Examiner* — Casey Hagopian
(74) *Attorney, Agent, or Firm* — Panitch Schwarze Belisario & Nadel LLP

(57) ABSTRACT

Calcium glycerophosphate is found to be effective in treating and preventing a disease, disorder and/or condition of the respiratory system. The disease, disorder and/or condition is related to an obstructive or a restrictive condition of the respiratory airway. The disease, disorder and/or condition can be a respiratory airway inflammatory disease, a respiratory airway stenosis or a nasal cavity inflammatory disease, such as an asthma, a chronic obstructive pulmonary disease (COPD), an emphysema, a reactive airway disease (RADS), rhinitis, bronchitis, bronchiolitis, congestion, sinusitis, tonsillitis, or laryngitis, post-nasal drip (PND) and a related complication thereof, inflamed degranulating and non-degranulating mast cell activity, any irritation occasioning mucus secretion from goblet cells breathing difficulty, restriction, obstruction; airways constriction or closure or mucus interference with air passage; sleep apnea, snoring, inflammatory or non-inflammatory responses to an airborne or non-airborne allergen or irritant; nasal or non-nasal airway inflammation or irritation caused by a problem in any area of the body; and a physical damage to the respiratory system. Methods, compositions and devices are described for using calcium glycerophosphate to treat and prevent the disease, disorder and/or condition of the respiratory system.

2 Claims, 17 Drawing Sheets

(56) References Cited

U.S. PATENT DOCUMENTS

| | | | |
|---|---|---|---|
| 5,547,946 A | | 8/1996 | Molinari |
| 5,603,943 A | * | 2/1997 | Yanagawa .................... 424/434 |
| 6,139,850 A | * | 10/2000 | Hahn et al. .................... 424/401 |
| 6,703,044 B1 | | 3/2004 | Pinhasi et al. |
| 2002/0081266 A1 | | 6/2002 | Woolfe et al. |
| 2003/0199594 A1 | * | 10/2003 | Shah ................................ 516/1 |
| 2004/0067920 A1 | * | 4/2004 | Leonard et al. ............... 514/178 |
| 2004/0197411 A1 | | 10/2004 | Gao et al. |
| 2006/0083691 A1 | * | 4/2006 | Wermeling ..................... 424/45 |
| 2007/0093553 A1 | * | 4/2007 | Baxter et al. .................. 514/557 |
| 2007/0190071 A1 | * | 8/2007 | Kurimoto et al. .......... 424/184.1 |

OTHER PUBLICATIONS

Int'l Preliminary Report on Patentability issued Mar. 2, 2010 in Int'l Application No. PCT/US08/74589.
Office Action issued Oct. 29, 2013 in CA Application No. 2701388.
Wu et al., "A Thermosensitive Hydrogel Based on Quaternized Chitosan and Poly(ethylene glycol) for Nasal Drug Delivery System", Biomaterials 28 (2007) 2220-2232.

* cited by examiner

CALCIUM GLYCEROPHOSPHATE FOR TREATING AND PREVENTING RESPIRATORY DISEASES OR CONDITIONS

CROSS-REFERENCE TO RELATED APPLICATIONS

This application is a continuation-in-part patent application of International Patent Application No. PCT/US08/74589, filed on Aug. 28, 2008, which was published as WO 2009/029705 on Mar. 5, 2009, titled "Calcium Glycerophosphate for Treating and Preventing Respiratory Diseases or Conditions," which claims the benefit of U.S. Provisional Patent Application No. 60/968,938, filed Aug. 30, 2007, the disclosure of which is herein incorporated by reference in its entirety. This application also claims the benefit of U.S. Provisional Patent Application No. 61/285,260, filed Dec. 10, 2009, the disclosure of which is herein incorporated by reference in its entirety.

BACKGROUND OF THE INVENTION

Diseases, disorders and/or conditions of the respiratory system occur commonly in both affluent countries and developing countries. They account for a significant proportion of all days of sickness related absence from work. The morbidity related to respiratory diseases, disorders and conditions has not decreased.

Therefore, there is a need to develop a relatively inexpensive means for treating and preventing diseases, disorders and/or conditions of the respiratory system. Preferably, such a means is non-toxic, non-hazardous and without significant side effects.

BRIEF SUMMARY OF THE INVENTION

It is now discovered that calcium glycerophosphate is effective in treating and preventing a disease, disorder and/or condition of the respiratory system.

In one general aspect, the present invention relates to a method of treating or preventing a disease, disorder and/or condition of the respiratory system in a subject. The method comprises administering to the respiratory system of the subject an effective amount of calcium glycerophosphate in a composition formulated for oral or nasal administration.

In another general aspect, the present invention relates to a composition for treating or preventing a disease, disorder and/or condition of the respiratory system in a subject. The composition comprises an effective amount of calcium glycerophosphate and is formulated for oral or nasal administration to the respiratory system of the subject by a nasal drop, a nasal spray, a gel, a nasal lavage, a quick-dissolving tablet, an inhaled powder, an oral inhalation solution or suspension, a syrup, a mechanized intermittent fluid pulser (such as Water-Pik®), an inhaler, a respirator, a transpirator, an atomizer, a vaporizer, a nebulizer, an air mask, an insufflator, a means for direct physical or mechanical application (such as a cotton swab), etc.

In yet another general aspect, the present invention relates to a device for treating or preventing a disease, disorder and/or condition of the respiratory system in a subject. The device comprises an effective amount of calcium glycerophosphate and a means for administering the effective amount of calcium glycerophosphate to the respiratory system of the subject.

Another general aspect of embodiments of the invention relates to a method of reducing, interdicting and/or repairing irritation to the respiratory system of a subject by an agent administered to the respiratory system of the subject, the method comprising:

1) administering the agent to the respiratory system of the subject; and
2) administering an effective amount of calcium glycerophosphate to the respiratory system of the subject, wherein the effective amount of calcium glycerophosphate reduces, interdicts and/or repairs irritation to the respiratory system of the subject by the agent.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments of the invention. It should be understood, however, that the invention is not limited to the precise arrangements and instrumentalities shown.

In the drawing.

DETAILED DESCRIPTION OF THE INVENTION

Figure 1:
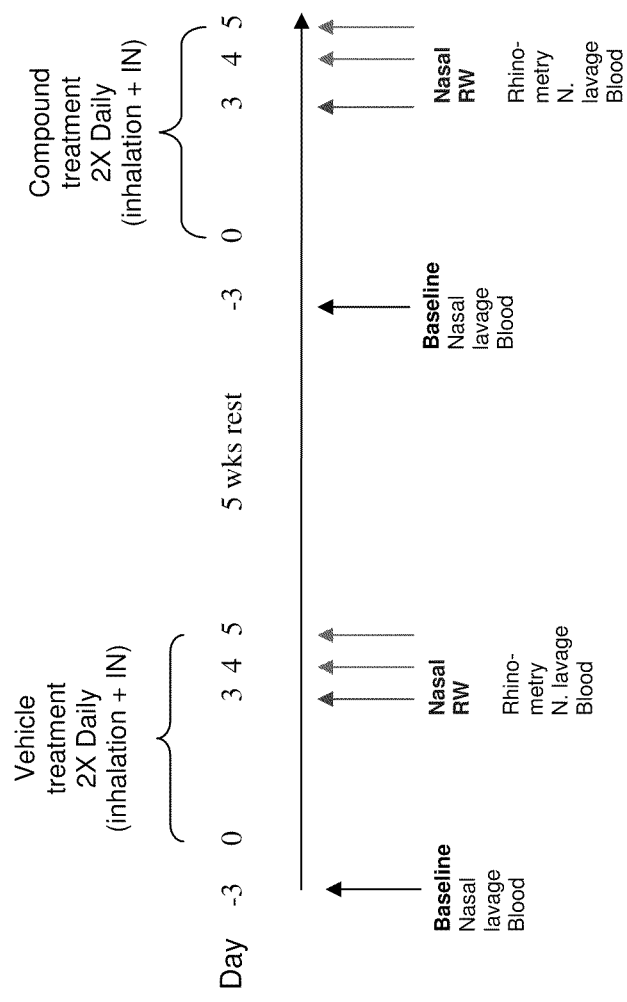
FIG. 1 summarizes the study design for characterizing the effects of CGP on rhinitis in ragweed sensitized Beagle dogs.

Calcium glycerophosphate has already been shown to behave as an anti-inflammatory substance on epidermal and epithelial cells and as a wound healer on epidermal cells as well as in the gums and mucosal soft tissue elsewhere in the body, e.g., vaginal. Investigation has been expanded to its use on the nasal mucosa and other parts of the respiratory system.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the term "subject" refers to a mammal, who has been the object of treatment, observation or experiment. Examples of a subject can be a human, a livestock animal (beef and dairy cattle, sheep, poultry, etc.), or a companion animal (dog, cat, horse, etc).

As used herein, the term "respiratory system" refers to all parts of the airway, i.e., the passageway for air during respiration, from the nose to the pulmonary alveoli. The respiratory system includes organs that are involved in breathing, such as the nose, throat, larynx, trachea, bronchi, and lungs.

As used herein, the term a "disease, disorder and/or condition of a/the respiratory system" refers to any disease, disorder and/or condition that is related to an obstructive or restrictive condition of a respiratory system. An obstructive condition of a respiratory system includes any condition which impedes the rate of air flow into and out of the lung. A restrictive condition of a respiratory system includes any condition which causes a reduction in the functional volume of the lung. The obstruction or restriction of the airway may cause symptoms such as wheezing, shortness of breath, difficulty breathing, chest tightness, and coughing. The disease, disorder and/or condition of the respiratory system can be, for example, an airway inflammatory disease, an airway stenosis, or a nasal cavity inflammatory disease.

Examples of the disease, disorder and/or condition of the respiratory system include, but are not limited to, an asthma; a chronic obstructive pulmonary disease (COPD); an emphysema, a reactive airway disease (RADS); rhinitis; bronchitis; bronchiolitis; congestion; sinusitis; tonsillitis; laryngitis; post-nasal drip (PND) and any and all complications dependent on same; inflamed degranulating and non-degranulating mast cell activity; any irritation occasioning mucus secretion from goblet cells or elsewhere, resulting in breathing difficulty, restriction and/or obstruction; airway constriction or closure or mucus interference with air passage; sleep apnea; snoring; inflammatory or non-inflammatory responses to any airborne or other allergen or irritant; nasal or other airway inflammation or irritation caused by any other body area problem; physical damage to the respiratory system such as nosebleed, surgery healing, traumatic injury; any respiratory disease, disorder and/or condition caused by an airborne or seasonal allergen or irritant, any swelling of tissue occasioned by any of the above, etc.

As used herein, the term "asthma" refers to a chronic condition, which in most cases is characterized by reversible airway obstructions and/or constrictions. The airway becomes inflamed and is lined with excessive amounts of mucus, often in response to one or more triggers for asthma. The triggers for asthma include, but are not limited to, an environmental stimulant, such as an allergen (ragweed, house dust, animal hair, pollen, etc.), cold air, warm air, moist air, change in temperature or humidity, upper respiratory infections, exercise, exertion, physical or emotional stress, smoke, viral illnesses such as those caused by common cold. The term "asthma" includes those caused by any cause of asthma whose primary effect is cellular inflammation and/or irritation, whether involving mast cells or not, degranulation or not, mucus exudation or not, whether exacerbant is identified or not, or whether the cause is airborne or not. The term 'asthma' is to be the widest-encompassing and is to include breathing difficulty of all degrees from the barely perceptible to acute.

Examples of asthma include, but are not limited to bronchial asthma, infantile asthma, allergic asthma, atopic asthma, steroid refractory asthma, non-allergic asthma, endogenous asthma, exogenous asthma, aspirin asthma, cardiac asthma, exercise-induced asthma, infectious asthma, any asthma triggered by airway restriction or constriction.

As used herein, the term "chronic obstructive pulmonary disease" or "COPD", also known as chronic obstructive airway disease (COAD), refers to a progressive respiratory disease characterized by limitation of airflow in the airway that is not fully reversible. COPD often involves permanent or temporary narrowing of small bronchi, in which forced expiratory flow is slowed. Examples of COPD include chronic bronchitis, emphysema and a range of other disorders to which no etiologic or other more specific term can be applied. COPD is most often due to tobacco smoking but can be due to other airborne irritants, such as coal dust, asbestos or solvents, as well as preserved meats containing nitrites.

As used herein, the term "reactive airway disease (RAD)" refers to an asthma-like syndrome developed after a single exposure to high levels of a trigger, such as irritating vapor, fume, or smoke. In a particular embodiment of the present invention, the term RAD includes an asthma-like syndrome in infants that may later be confirmed to be asthma when they become old enough to participate in diagnostic tests.

As used herein, the term "rhinitis" refers to any disease, disorder and/or condition caused by inflammation of the nasal mucous membrane. Examples of rhinitis include, but are not limited to, allergic rhinitis, pollinosis, acute rhinitis, chronic rhinitis, hypertrophic rhinitis, deflected septum and the like. Symptoms of rhinitis include, but are not limited to, a runny nose, nasal congestion and post-nasal drip. According to recent studies completed in the United States, more than fifty million Americans are current sufferers of rhinitis. Rhinitis has been found to adversely affect more than just the nose, throat, and eyes. It has been associated with sleeping problems, problems with the ears, and has even been linked to learning problems. Causes that may bring about the presence of rhinitis include food reactions, anatomic defects, immunodeficiency diseases, ciliary dyskinesia, environmental triggers, emotional triggers, occupational triggers, hormonal triggers, etc.

As used herein, the term "calcium glycerophosphate" or "CGP," also known as "glycerophosphate calcium," refers to a chemical compound having a molecular formula of $C_3H_7CaO_6P$ in its anhydrous form. "CGP" can also exist as a hydrate, including the monohydrate and the dihydrate. Examples of calcium glycerophosphate include, but are not limited to, any one, or any combination of two or more of the three isomers of CGP, namely β-glycerophosphoric acid calcium salt $((HOCH_2)_2CHOPO_3Ca)$ and D(+) and L(−)-α-glycerophosphoric acid calcium salt $(HOCH_2CH(OH)CH_2OPO_3Ca)$.

Calcium glycerophosphate can be synthesized using methods known in the art. Calcium glycerophosphate can also be obtained from various commercial sources. The commercially available CGP preparations include, but are not limited to, those available from AkPharma Inc. (Pleasantville, N.J. 08232), Astha Laboratories Pvt, Ltd, (B-4, Industrial Estate, Sanathnagar, Hyderabad-18, India), and Seppic Inc. (30 Two Bridges Road, Fairfield, N.J. 07004).

As used herein the term "treatment", "treat" or "therapy" refers to the prevention of deterioration of a disease, disorder or condition when a patient contracts such a disease, disorder or condition, preferably, at least maintenance of the status quo, and more preferably, alleviation, still more preferably, resolution of the disease, disorder or condition.

As used herein the term "prophylaxis", "prevent" or "prevention" refers to, when referring to a disease, disorder or condition, a type of treatment conducted before such a disease, disorder or condition occurs such that the disease, disorder or condition will not occur, will be delayed to occur, or will occur but will deteriorate to a less degree.

As used herein, the term "treat" or "prevent" in the broadest sense, with respect to a disease, disorder or condition, refers to any medical act thereto, and include any act for diagnosis, therapy, prevention, prognosis and the like.

When used for treating or preventing a disease, disorder and/or condition of the respiratory system, calcium glycerophosphate can be used as a reliever which is used during an episode or an attack of the disease, disorder and/or condition, such as an episode of an asthma, for alleviation of the episode or attack. Calcium glycerophosphate can also be used as a controller which is used for long-term control to prevent the occurrence of the episode or attack. Controlling or preventing an attack is substantially the therapy of a disease, disorder and/or condition of the respiratory system per se, because it is equally important to control and prevent an attack as to relieve or alleviate the attack. Those skilled in the art will be able to use an appropriate dosage of calcium glycerophosphate for either therapy or prevention of a disease, disorder and/or condition of the respiratory system.

The term "effective amount" as used herein means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. The administration of an effective amount of calcium glycerophosphate to a subject results in a clinically observable beneficial effect. The clinically observable beneficial effect can be a situation in which an observable disease, disorder and/or condition of the respiratory system is prevented from further development or aggravation or will develop to a lesser degree, than without administration of the composition of the present invention. The clinically observable beneficial effect can also be a situation in which a disease, disorder and/or condition of the respiratory system is prevented from occurring or subsequently occurs to a lesser degree than without administration of the composition of the present invention, when the composition is administered to a subject before the disease, disorder and/or condition of the respiratory system is observable. In one embodiment of the invention, an effective amount of calcium glycerophosphate alleviates or improves a disease, disorder and/or condition of the respiratory system in a subject to a degree that is about any of 10%, 20%, 30%, 40%, 50%, 60%, 70%, 80%, or 90% of that which would have been had the subject not received an effective amount of calcium glycerophosphate.

Methods are known in the art for determining therapeutically and prophylactically effective doses of calcium glycerophosphate according to embodiments of the present invention. A useful assay for confirming an effective amount (e.g., a therapeutically effective amount) for a predetermined application is to measure the degree of recovery from a target disease. An amount actually administered depends on an individual to be treated. The amount is preferably optimized so as to obtain a desired effect without significant side effects. The determination of a prophylactically or therapeutically effective dose is within the ability of those skilled in the art. A prophylactically or therapeutically effective dose of any compound can be estimated using either a cell culture assay or any appropriate animal model. The animal model is used to achieve a desired concentration range and an administration route. Thereafter, such information can be used to determine a dose and route useful for administration into humans.

The therapeutic effect and toxicity of a compound may be determined by standard pharmaceutical procedures in cell cultures or experimental animals (e.g., $ED_{50}$, a dose therapeutically effective for 50% of a population; and $LD_{50}$, a dose lethal to 50% of a population). The dose ratio between therapeutic and toxic effects is a therapeutic index, and it can be expressed as the ratio of $LD_{50}/ED_{50}$. Pharmaceutical compositions which exhibit high therapeutic indices are preferable. The data obtained from cell culture assays and animal studies can be used for formulating a dosage range for use in humans. The dosage of such compounds lies preferably within a range of circulating concentrations that include the $ED_{50}$, with little or no toxicity. Such a dosage may vary within this range depending upon the dosage form employed, the susceptibility of a patient, and the route of administration. Guidance for specific doses and delivery methods is provided in publications known in the art. The exact dose is chosen by an individual physician in view of the condition of a patient to be treated. Doses and administration are adjusted to provide a sufficient level of the active portion, or to attain a desired effect.

The effective amount of CGP can be any dosage amount, from micro-doses to mega-doses. Mega-doses of CGP can be effectively used, because CGP is non-toxic, non-hazardous and has no known side effects. Micro-doses of CGP can be effectively used, because both $Ca^{2+}$ and the glycerophosphate anion are signaling molecules that can have a biological effect at very low levels.

In embodiments of the present invention, the effective amount of CGP is administered to the subject in a composition containing about 0.05%-15% (w/w), preferably about 0.5%-10% (w/w); most preferably about 1%-5% (w/w) of CGP. It has been discovered that at higher levels tested, e.g., about 7.5% (w/w) or above, calcium glycerophosphate may help in stanching nosebleeds, possibly due to the effect of calcium on blood clotting. However, the amount of CGP in the composition is not limited to about 0.05%-15% (w/w).

In one general aspect, an embodiment of the present invention relates to a method of treating or preventing a disease, disorder and/or condition of a respiratory system in a subject. The method comprises administering to the respiratory system of the subject an effective amount of calcium glycerophosphate, wherein calcium glycerophosphate is administered to the respiratory system of the subject in a composition formulated for oral or nasal administration. The composition formulated for oral or nasal administration can be a liquid, solid, gel, syrup, powder, or mist formulation.

Calcium glycerophosphate can be administered to the respiratory system of the subject by one or more means of oral or nasal administration depending on the type of diseases, disorders and/or conditions of the respiratory system. For example, in the case of asthma, COPD and the like, atomizer type inhalators such as MDI, BDI, or nebulizers and the like may be used for inhalation. For example, in the case of rhinitis, absorption and inhalation may be used for administration. Examples of applicable means of oral or nasal administration include, but are not limited to, a nasal drop, a nasal spray, a nasal lavage, a quick-dissolving tablet, an inhaled powder, an oral inhalation solution or suspension, a syrup, a mechanized intermittent fluid pulser (such as Water-Pik®), an inhaler, a respirator, a transpirator, an atomizer, a vaporizer, an air mask, an insufflator, a means for direct physical or mechanical application, such as a cotton swab, etc.

Inhalation is conventionally used as a method for administration via the nasal cavity, airway and nasal pathways and the like. In intra-airway administration formulations, transairway absorption formulations or pernasal absorption formulations, it is usually preferable to make a drug solution in a mist form or as fine powder (dry powder). Generally, a drug solution formed may be inhaled by means of a nebulizer, those processed into powder may be inhaled by means of a gas-atomizing type, MDI (metered dose inhaler) or expiration inhalation system, DPI (dry powder inhaler) with the drug loaded therein.

With respect to powder inhalers, there are two types presently used for rapid and deep inhalation, "dry powder inhaler (DPI)" and delayed inhaling type "metered dose inhaler (MDI)". DPI are further classified into three categories: multi-dose reservoir, such as the product TURBUHALER®, available from AstraZeneca; multi-unit dose, such as the product ACCUHALER™/FLOVENT DISKUS™, Advair™, available from GSK; and unit dose, available from many manufacturers.

Inhaler refers to a kit comprising a mouth piece and cartridge (tube), and are usually employed by sealing both termini of the tube with aluminum foil. Prior to use, the tube is equipped with the mouth piece to pierce the aluminum foil, thereby allowing inspiration of powdered drug inside.

On the other hand, absorption of a drug solution may be achieved by means of a nebulizer or respirator, an artificial respirator. A nebulizer causes a drug aerosol to flow in the air at slow speed, thus makes it easier for one to absorb the drug.

How often and how long calcium glycerophosphate is administered to a subject depends on the disease, disorder and/or condition of the respiratory system to be treated or prevented, as well as factors associated with the subject, e.g., age, weight, health, etc. Calcium glycerophosphate can be administered on a regimen of one to multiple times per day. Calcium glycerophosphate can be administered to the subject at intervals during the day, such as upon arising, after breakfast, lunch, dinner, and upon retiring. Calcium glycerophosphate can be administered during an episode or an attack of the disease, disorder and/or condition of the respiratory system to provide a relief of symptoms, such as wheezing, shortness of breath, difficulty breathing, chest tightness, and coughing. Calcium glycerophosphate can also be administered to a subject prior to an episode or an attack to control or prevent the episode or attack and the symptoms associated with the episode or attack.

Dosages of calcium glycerophosphate are not limited to a particular value. The dosage appropriately varies depending on the targeted disease, condition (extent), age, the presence or absence of complication(s), etc. For example, the dosage is usually, per adult, per administration, about 100 μg to about 1000 mg, preferably about 500 μg to about 100 mg, and most preferably about 1 mg to about 40 mg of anhydrous CGP. As used herein, "anhydrous CGP" refers to a CGP preparation that contains at least about 88% (w/w) of CGP that is free of residual or acquired moisture. The anhydrous CGP used in embodiments of the present invention complies with Food Chemicals Codex (FCC) specifications, in which loss on drying (LOD) is not to exceed 12%. As used herein, "per administration" can be, per inhalation per nostril, per spray, per tablet, etc. In one embodiment of the present invention, the dosage is about 400 mg solution/suspension formulation containing about 2% by weight of dry CGP per administration. In another embodiment of the present invention, the dosage is about 400 mg solution/suspension formulation containing about 3.75% by weight of dry CGP per administration. The dry CGP contains about 95-98% anhydrous CGP balancing with moisture. However, the dosage of CGP is not limited to the above ranges and can be any range without causing physical endangerment.

While not wishing to be bound by theory, calcium glycerophosphate can be used to treat or prevent a disease, disorder and/or condition of the respiratory system at least in part due to the anti-inflammatory effect of CGP. Inflamed airway epithelium results in a disease, disorder and/or condition of the respiratory system. Various observations suggest that a glycerophosphate salt functions to promote epidermal cell renewal, see for example, US2004/0037766. The quick repair and replacement of epidermal cells provide, among other things, enhanced ceramide synthesis, which hastens repair of the skin's surface and provides tighter cell-to-cell adhesion, which may prevent invasion between vulnerable cell walls of irritating substances. This is to be distinguished from the possible function of the calcium ion to modify the permeability of cell membranes, per se, i.e., the ability of calcium ion to decrease membrane porosity at a large concentration. The reduction, interdiction, suppression or prevention of inflammation of the respiratory system provides symptom relief or prevention. The beneficial effect of CGP may also be due to, at least in part, its ability to prevent or reduce acid-caused irritation and cytotoxicity in the upper and lower respiratory tract, and/or its ability to promote higher ciliary activity, e.g., via regulating the phosphorylation state of certain ciliary proteins. It is believed that the newly discovered beneficial effect of CGP on the respiratory system according to embodiments of the present invention is achieved synergistically between the calcium ion and the glycerophosphate. This synergistic effect is distinct from the function of the calcium ion or the glycerophosphate alone.

Calcium glycerophosphate is non-toxic, non-hazardous and has no known side effects. Therefore, methods according to embodiments of the present invention are particularly desirable for pediatric patients, elderly patients, pregnant women, or patients who have frequent need of relief medications and/or preventive medications for a disease, disorder and/or condition of the respiratory system. Oral or nasal administration of the composition according to the present invention is non-invasive and can be repetitively provided.

In particular embodiments, calcium glycerophosphate can be administered in combination with one or more other relief and/or preventive agents for a disease, disorder and/or condition of the respiratory system. Thus, embodiments of the present invention relate to compositions comprising calcium glycerophosphate and one or more other relief and/or preventive agents for a disease, disorder and/or condition of the respiratory system, and methods of using the compositions for treating or preventing a disease, disorder and/or condition of a respiratory system in a subject. Calcium glycerophosphate and the other agent can be administered simultaneously or sequentially, one following the other. The other agents can be administered to the subject via routes of administration customarily used for such other drugs. However, it is not necessary to administer the other relief and/or preventive agent in a substantial percentage of instances according to embodiments of the present invention. Calcium glycerophosphate, as the sole active pharmaceutical ingredient, is effective to treat or prevent a disease, disorder and/or condition of the respiratory system.

Examples of such relief and/or preventive agents include, but are not limited to, a beta-2 agonist, a long-acting beta-2-agonist ("LABA"), an inhaled corticosteroid, an alpha agonist, a bronchodialator, a glucocorticoid, a leukotriene modifier, a mast cell stabilizer, an antimuscarinic/anticholinergic, a methylxanthine, an antihistamine, omalizumab, methotrexate, and tianeptine, albuterol, cromolyn, or the like. Examples of LABA include, for example, salmeterol, formoterol, bambuterol, clenbuterol, and indacaterol.

Other embodiments of the present invention relate to compositions comprising calcium glycerophosphate and one or more analgesics, and methods of using the compositions for treating or preventing a disease, disorder and/or condition of a respiratory system in a subject. Examples of the compositions include, but are not limited to, a pharmaceutical product for treating a cold, hayfever, any respiratory disease, disorder and/or condition caused by an airborne or seasonal allergen or irritant, etc., comprising CGP as the nasal cleaner/decongestant (NasoCell™) and a common over the counter (OTC) analgesic such as ibuprofen, acetaminophen, aspirin, naproxen, capsaicin, etc. The amount of CGP in the composition can be appropriate to supply in a single dosage, which may be 2 to 4 sprays of the NasoCell, to provide nasal cleaning and/or decongestant. The amount of the analgesic in the composition can be effective to relieve common headaches, sinus aches, eye aches, etc. that are associated with colds, hay fever, etc.

Nasal administration of the composition according to the present invention can provide more rapid relief of the symptoms associated with cold, hayfever, etc. Administration via nasal membrane absorption can be more quantitatively effective and more chronologically prompt to reach the bloodstream than the same analgesic ingested that must go through the gastric system for subsequent absorption with possible compositional compromise by the digestive process. In addition, the hypotonicity of the NasoCell allows the composition to adhere more readily to the epithelial nasal cells, thus be absorbed more readily through the cell walls and into the bloodstream.

The compositions according to the present invention offer the unique combination of effective nasal cleaning, nasal clearing, anti-inflammation, anti-swelling, and pain relief, without any of the psychogenic effects associated with the presently marketed drugs, such as diphenhydramine, ephedrine, pseudoephedrine, etc., nor any of the undesirable, typical anti-cholinergic side effects at the site or elsewhere in the body. The composition is safe to use liberally even when driving or operating machinery.

In another general aspect, an embodiment of the invention provides a composition for treating or preventing a disease, disorder and/or condition of the respiratory system in a subject. The composition comprises an effective amount of calcium glycerophosphate, wherein the composition is formulated for oral or nasal administration to the respiratory system of the subject by a nasal drop, a nasal spray, a nasal lavage, a quick-dissolving tablet, an inhaled powder, an oral inhalation solution or suspension, an inhaler, a respirator, a nebulizer, a transpirator, an atomizer, a vaporizer, an air mask, an insufflator, a means for direct physical or mechanical application, such as a cotton swab, etc.

Agents for treating or preventing diseases or disorders other than respiratory diseases or disorders can also be administered through the respiratory system, such as by nasal administration, because such route of administration provides faster and more direction absorption of the agent into the blood stream. However, some of the agents may cause irritation or inflammation to the respiratory system. Thus, another general aspect of embodiments of the invention relates to a method of reducing, interdicting and/or repairing irritation to the respiratory system of a subject by an agent administered to the respiratory system of the subject. The method comprises 1) administering the agent to the respiratory system of the subject; and
2) administering an effective amount of calcium glycerophosphate to the respiratory system of the subject, wherein the effective amount of calcium glycerophosphate reduces, interdicts and/or repairs irritation to the respiratory system of the subject by the agent.

The agent and CGP can be administered simultaneously or sequentially, one following the other. The agent and CGP can be administered in one or separate formulations for respiratory system administration.

In an embodiment of the present invention, the method of reducing, interdicting and/or repairing irritation to the respiratory system of a subject by an agent administered to the respiratory system of the subject comprises:

1) providing a formulation for respiratory system administration comprising the agent and an effective amount of calcium glycerophosphate; and
2) administering the formulation to the respiratory system of the subject, wherein the effective amount of calcium glycerophosphate reduces, interdicts and/or repairs irritation to the respiratory system of the subject by the agent.

The formulation can be any formulation administrable to the respiratory system of the subject. In an embodiment of the present invention, the formulation is a nasal formulation comprising a therapeutic agent and an effective amount of CGP. In another embodiment of the present invention, the formulation is for oral inhalation administration that comprises a therapeutic agent and an effective amount of CGP. The effective amount of CGP reduces, interdicts and/or repairs irritation to the respiratory system of the subject by the therapeutic agent The formulation is administered to the respiratory system of the subject by a nasal drop, a nasal spray, a nasal lavage, a quick-dissolving tablet, an inhaled powder, an oral inhalation solution or suspension, a syrup, a mechanized intermittent fluid pulser, an inhaler, a respirator, a transpirator, an atomizer, a vaporizer, an air mask, a nebulizer, a means for direct physical or mechanical application, or an insufflator.

The composition according to embodiments of the present invention may be produced using a method similar to methods known in the art, e.g., conventional mixing, dissolution, rendering to granules, preparation of a sugar-coated agent, elutriation, emulsification, capsulation, inclusion, or freeze drying. One or more excipients can be added to the composition. Excipients which can be used are those that are inactive against calcium glycerophosphate, and as long as the use is recognized as a pharmaceutical additive, no limitation is made for such excipient. Examples of appropriate excipients include, but are not limited to, monosaccharides such as galactose, mannose, sorbose; disaccharides such as lactose, sucrose and trehalose and the like; polysaccharides such as starch, raffinose, dextran and the like; sugar alcohols (including glycerol, erythritol, arabitol, xylitol, sorbitol, mannitol); glycols (including ethylene glycol, propylene glycol, polyethylene glycol, polypropylene glycol); cellulose-like polymers (including hydroxy cellulose, hydroxy propyl cellulose); insoluble additives (crystalline cellulose, chitosan, calcium carbonate, talc, titanium oxide or silica (silicon oxide), and mixtures thereof.

The composition according to embodiments of the present invention can be formulated to have a pH of about 4.5-10, such as about 4.5-6.0, about 6.0-7.0, about 7.0-8.0, about 8.0-9.0, about 7.0-9.0, about 7.5-9.0, or about 8.0-10.0. Note that nasal pH varies considerably, from 4.5-6.5 in normal nasal cells, to as high as 8.3 in rhinitis. However, the pH of the composition according to embodiments of the present invention is not limited to the range of about 4.5-10, or that of the nasal pH.

The composition according to embodiments of the present invention can further contain a preservative. Preferably the preservative is food grade or pharmaceutical grade. Examples of appropriate preservatives include, but are not limited to, methylparaben, ethylparaben, butylparaben, propylparaben, sorbic acid and any other preservative that is typically used in water-based cosmetics, such as creams and lotions and some bath products. The preservative is preferably present at an amount that is sufficient to prevent the composition from supporting the growth of microbes, such as bacteria, fungi, or yeasts.

The composition according to embodiments of the present invention can also include an adhesion molecule or material that allows the composition to adhere to an airway tissue for an extended period of time, thus results in an extended release of CGP into the airway. Adherence is accomplished by a number of interactions, physical or chemical, such as electrostatic interaction, hydrogen bonding or hydrophobic interaction. In preferred embodiment, the adhesion molecule or material extends the contact time of CGP in the nasal cavity. Any suitable adhesion molecule or material known to a person skilled in the art can be used in a composition according to embodiments of the present invention. In one embodiment, the adhesion molecule or material is a polysaccharide. In a preferred embodiment, the adhesion molecule is chitosan, a cationic polysaccharide derived from the shells of crustaceans. A versatile transmucosal delivery system based on chitosan is commercially available from West Drug Delivery of Lionville, Pa. 19353 (US), and can be used in the present invention.

In a preferred embodiment, the composition of the present is formulated as a powder, gel, microsphere, or suspension, i.e., liquid comprising CGP in an amount exceeding the solubility of CGP in the liquid. CGP has limited solubility in water, i.e., about 1% by weight. Administration of CGP in a formulation of powder, gel, microsphere, or suspension can result in a local amount of CGP exceeding its solubility, thus deposition of insoluble CGP onto the mucous membranes of the respiratory system. As the insoluble CGP slowly dissolves into mucous membranes, an extended release of CGP into the cells lining the airway is achieved without the need for any additional assisting adhesion substances. Optionally, the powder, gel, microsphere, or suspension formulation can include an adhesion molecule, a "sticker", or material that further enhances the CGP's adherence to the airway mucosal surface.

A formulation that provides an extended release of CGP is preferred, for example, when it is desirable to provide a sustained and steady state level of CGP into the respiratory system for an extended time period, such as when the formulation is used for prophylaxis. In one embodiment, a method according to embodiments of the invention comprises administering to the respiratory system of the subject a formulation that provides an extended release of CGP into the airway. In a preferred embodiment, the CGP is released into the airway during a time period of 3-8 hours.

In another embodiment, a composition according to embodiment of the present invention comprises an absorption enhancer that improves absorption of CGP into the airway, e.g., across the mucous membranes of the airway. There are a number of ways an absorption enhancer can act. For example, it may alter properties of the mucus layer by opening tight junctions between the cells, or it may increase membrane fluidity. Any suitable absorption enhancers known to a person skilled in the art can be used in a composition according to embodiments of the present invention. A formulation that provides an improved absorption of CGP is preferred, for example, when it is desirable to provide an immediate and high level of CGP into the respiratory system, such as when the formulation is used for treatment during an episode or an attack. In one embodiment, a method according to embodiments of the invention comprises administering to the respiratory system of the subject a formulation that provides an improved absorption of CGP into the airway.

The composition according to embodiments of the present invention can be formulated in various forms that are suitable for oral or nasal administration in view of the known technologies in the art. For example, a form of spray or expiration adapted format including microparticles, such as dry powder, can be used for intra-airway administration or transairway absorption. Dry powder may be manufactured by means of one selected from the group consisting of a bowl mill, a bead mill, a jet mill, an ultimizer, a mortar, a stonemill, spray drying and supercritical fluid. The aerodynamic average particle size of the dry powder may be optimized for administration, e.g., to allow the powder to float freely in an airstream, settle and adhere to exposed mucosal cell membranes. For airway administration, it is desirable that the aerodynamic average particle size of dry powder is typically about 0.01 to about 50 μm, preferably, about 0.1 to about 30 μm, still preferably about 0.1 to about 10 μm, in diameter. For pulmonary administration, in view of the delivery into the alveoli pulmonis, those particles having an aerodynamic average particle size of about 3 μm or less are preferably manufactured, but the present invention is not limited thereto. The powders can be inhaled or inspired. They can be dispensed via a "puff" container of any sort, including those which dispense unmetered or metered amounts.

A composition according to an embodiment of the present invention can be associated with an aerosol system, such as an aerosol spray can. The aerosol system includes, for example, vessels with propellant included therein. The propellant comprises the active ingredient CGP and conventional additives such as lactose. The formulation of the propellant determines the properties of the output of the aerosol system, such as particle distribution, delivery rate, viscosity and the like. Such aerosol systems can be manufactured using methods known in the art in view of the present disclosure.

A composition according to an embodiment of the present invention can also be an aqueous solution/suspension, which is suitable for nasal cavity administration or for inhalation, such as by direct nasal lavage, liquid stream or spray. The solution is atomized to very small particles of a size range of 1-10 μm. An aerosol finely distributed within an atomized solution can also be inhaled. Detailed information relating to aerosol inhalants is available, for example, from a pharmacopoeia such as the Japanese Pharmacopoeia, US Pharmacopoeia and the like, which are herein incorporated hereby as references in their entirety. The aqueous solution/suspension can be sprayed under hand-operated actuation, such as in a squeezable bottle or plunger, or it can be in a pressurized container.

A composition according to an embodiment of the present invention can further be a gel or cream for nasal application, in which case the ingredients would have, in addition to those described above, suitable stabilizing substances to raise the viscosity to desired levels. Examples of such stabilizing substances include, but are not limited to, sodium carboxymethyl cellulose gum (CMC gum), guar gum, xanthan gum, etc. A composition according to an embodiment of the present invention can further comprise fatty acids of vegetable source or of animal source, such as butyric acid.

In a particular embodiment of the present invention, the composition is an aqueous solution/suspension comprising about 1-5% (w/w) CGP; one or more acceptable moisturizers, such as glycerol, sorbitol and/or the like; one or more acceptable bacteriostats/mycostats, such as methyl paraben, grapefruit seed extract or the like; one or more flavorings or aromatics, such as vanilla, eucalyptus or the like, and purified, sterile water. Such a composition is applied to the respiratory system by direct nasal lavage or nasal or oral inhalation.

In another particular embodiment of the present invention, the composition is an aqueous solution/suspension comprising about 6-10% (w/w) CGP; one or more acceptable moisturizers, such as glycerol, sorbitol and/or the like; one or more acceptable bacteriostats/mycostats, such as methyl paraben, grapefruit seed extract or the like; one or more flavorings or aromatics, such as vanilla, eucalyptus or the like; purified, sterile water; a stabilizing or thickening agent; and an adhesion molecule. Such a composition is applied to the nasal cavity as a nose drop.

In another aspect, the present invention provides a device for treating or preventing a disease, disorder and/or condition of the respiratory system in a subject. The device comprises an effective amount of calcium glycerophosphate and a means for administering the effective amount of calcium glycerophosphate to the respiratory system of a subject. It should be understood that such a device may be in any format as long as the device is for facilitating the administration of calcium glycerophosphate to the respiratory system. The means for administration to the respiratory system comprises means selected from the group consisting of means for administration to the lung, means for transairway administration, means for transairway absorption and means for nasal absorption.

Exemplary means for administration to the airway include, but are not limited to, an inhaler, a respirator, a transpirator, an atomizer (e.g., a means to apply a spray/mist from a container such as a squeezed bottle or pressure container), a vaporizer, an air mask, an insufflator, and a means for direct physical or mechanical application. In particular embodiments, the means for administration to the airway is a metered dose inhaler (MDI), a dry powder inhaler (DPI), a nebulizer, a means for performing direct nasal lavage, a cotton swab, etc.

Exemplary means for administration to the lung include, but are not limited to, an inhaler and a bronchoscope, including those bronchoscope systems commercially available from Olympus Inc.

EXAMPLE 1

Effectiveness of Calcium Glycerophosphate in Sensitized Brown-Norway Rats

Animal models of asthma can be used to demonstrate the effectiveness of CGP on asthma. The Brown-Norway (BN) rat model of airway hyperresponsiveness (AHR) has been shown to possess features similar to human allergic asthma, such as early- and late-phase reactions after allergen challenge and the development of an IgE response to allergic sensitization (Haczku et al., *Immunology.* 85(4):598-603 (1995)). Such BN AHR rats can be produced by sensitization and exposure to ovalbumin (OVA) following a method similar to that described in *Eur J. Pharmacol.* 7; 293(4):401-12 (1995) or Haczku et al. (1995), above. CGP can be administered to the BN AHR rat prior to or after irritating the BN AHR rats with OVA. The airway responsiveness can be measured prior to or after CGP administration.

Brown Norway rats (8-10 weeks old; weight: 150-300 g) are bred and maintained by adhering to standards/guidelines established by the Association for Assessment and Accreditation of Laboratory Animal Care ("AAALAC"). These rats are sensitized by giving 4 mg of aluminum hydroxylate and 1 mg ovalbumin (OVA; Sigma, grade V) in one ml of pyrogen-free saline by cervical subcutaneous injection for sensitization. *Bordetella pertussis* vaccine containing $3 \times 10^9$ heat inactivated bacteria is used for intraperitoneal injection as an adjuvant. As a control, the same solution described above but without ovalbumin is intraperitoneally injected, thus providing a negative control. About 10-15 days after sensitization, airway irritation is induced by challenging the rats with 5-10% aerosolized OVA for 5-10 min using a nebulizer. Aerosol exposure can be accomplished by placing the rats in a plexiglass chamber connected to a nebulizer, which generates an aerosol mist pumped into the exposure chamber by the airflow supplied by a small animal ventilator set at 60 strokes/min, with a pumping volume of 10 ml.

CGP can be administered to the rats by nasal inhalation (using an aerosol or a powder), or intubation (liquid, aerosol, respirator), either before or after the airway irritation is induced.

Airway responsiveness of the rats can be measured. Anaesthetized, tracheostomized and ventilated rats are monitored for their airflow, transpulmonary pressure and blood pressure. Lung resistance is simultaneously calculated using known method, such as a software program (LabView, National Instruments, Austin, Tex.). Bronchial Alveolar Lavage (BAL) fluid is collected. BAL is performed using 5 ml of phosphate buffered saline (PBS; 137 mM NaCl, 10 mM sodium phosphate buffer pH 7.4, 2.7 mM KCl), 4 times. The total number of cells in BAL fluid can be determined using an erythrocytometer and the percentage of eosinophils in BAL fluid can be determined by differential cell counting.

An OVA challenge will elicit a statistically significant increase in infiltration of inflammatory cells mainly consisting of eosinophils in the airway. The ability of CGP to suppress the increase of eosinophils in BAL fluid in response to the OVA challenge will be measured. The effectiveness of CGP can be studied at various dosages, in various formulations, at various pH, etc., together with proper control formulations.

EXAMPLE 2

Effectiveness of Calcium Glycerophosphate in Allergic Rhinitis Animal Models

Animal models of rhinitis can be used to demonstrate the effectiveness of CGP on rhinitis. Methods are known to produce animal models of rhinitis. For example, a mouse model of allergic rhinitis can be developed by local sensitization of mice with *Dermatophagoides pteronyssinus* (Kim et al., *Otolaryngol Head Neck Surg.* 2007 May; 136(5):720-5); and a guinea pig model of rhinitis can be developed by bilateral intranasal sensitization of guinea pigs with the instillation of cedar pollen extracts (Mizutani et al., *Jpn J Pharmacol.* 2001 June; 86(2):170-82).

CGP can be administered to the animal models of rhinitis via desirable means such as inhalation or spray. Symptoms of rhinitis, nasal mucosa eosinophilia, serum total IgE, cytokines, and eosinophilia in BAL fluid of the animal models are measured before or after CGP administration in order to evaluate the effectiveness of CGP.

EXAMPLE 3

Applications of Calcium Glycerophosphate to a Human Subject Having a Respiratory Condition Investigation of the effectiveness of a calcium glycerophosphate for treating or preventing a disease, disorder and/or condition of the respiratory system has now been extended further to the human body.

CGP was incorporated into samples of a lavage or a spray product at varying concentrations, along with different sweetening/moisturizing components (sorbitol, glycerin) at varying levels (0.5% to 7.5% by weight), appropriate food/drug grade fungistats and bacteristats (methyl paraben and benzalkonium chloride), and light flavorings of several types (peppermint, spearmint and orange) in some iterations.

A first human subject for laboratory/home trials was a 77 year-old man in good general health. The subject has a life history of childhood asthma, which is currently inactive except for rare mild adult episodes, all of which occurred several years prior, deviated septum blocking of one nostril ~60%. The subject has a history of childhood allergies to ragweed, house dust, horse hair, etc., but these are inactive at present. The subject has experienced a decades-long post nasal drip (PND) as an adult, nasal obstruction (mucus, septum). The subject has experienced coughs that have been of weeks-long and, on occasion, months-long duration, following seasonal flu or colds. The subject has experienced chronic throat-clearing from PND and chronic cough even when not post-respiratory illness, which he ascribes to bronchitis. This results in occasional inconvenience when the subject has had to excuse himself from a group to clear out throat elsewhere, including spitting out or reflexive swallowing of the mucus which will on occasion roughen voice. The subject breathed almost exclusively through mouth as a child because of nasal obstruction. The subject breathes through both nose and mouth as an adult, with breathing through nose occasionally mildly problematic, requiring active conscious engagement, although the subject was never "short of breath" in terms of lung capacity, etc.

Forced Nasal Lavage Experiment

The subject performed forced nasal lavage once daily for about two weeks. The forced nasal lavage was conducted intranasally over skin and normally in a shower. An aqueous solution or suspension of CGP at various concentration, such as about 7.5%, 3.75%, 2.5%, 2%, 1.5% by weight of dry CGP, was forced into one nostril and out of the other nostril using a closed plastic bottle with an internal stem feed. This procedure was repeated for each side of the nostrils. Some product was swallowed via nasal route and there was approx. 2 oz. fluid per nostril.

Within about 0-10 minutes after the lavage, the subject experienced considerable drainage fore and aft the nasal passages, considerable throat-clearing, and very wet nasal passages. The subject spit out some swallowing. Within about 10-20 minutes after the lavage, the subject experienced 90% decreased drainage, open and drying nasal passages, and easier breathing. Within about 20-60 minutes after the lavage, the subject felt that nasal passages remained open and drying, voice was clearer and throat-clearing was about 90% diminished compared with prior state. Within about 1 hr to 12/24 hr after the lavage, the subject experienced no drip, no cough, and easy open breathing. He could breathe naturally through his mouth and nose without active conscious engagement. His lower airway passages opened fully.

Spray/Mist Experiments

The subject applied CGP into his nostrils in a spray or a mist. A closed small plastic bottle with internal stem feed constructed to deliver fluid contents as mist was used. Typically, one application was performed in the morning. Each application consisted of two sprays per nostril, alternating sides, with full simultaneous deep breath inhalation or inspiration to draw the product up the nose and into the airway passages. The spray was also, on occasion, applied directly through the mouth to the throat with 1 or 2 sprays per application. An average spray delivery contained about 200 mg of a formulation of CGP per squeeze. The formulation contained about 2% to about 3.75% by weight of dry CGP.

The subject experienced benefits from the nasal spray essentially the same as those of lavage but without all the preliminary hydraulics and recovery from same. CGP exerted its relieving effects almost instantaneously upon application and the benefits lasted about four to eight hours post application. The spray/mist application was repeated occasionally in the afternoon or as needed. It was observed that a single spray per nostril at bedtime appeared to produce better night breathing. The spray/mist application was much neater, easier to operate, more portable, and more feasible for regular use.

After administration of the CGP to the respiratory system, either via forced nasal lavage or spray/mist, the subject experienced about 95-98% reduction of post nasal drip, a daily nuisance to subject whether upright and active or reclining, complete cessation of coughing, open breathing through his nose without any, or at worst, with minimal restriction.

In addition to the routine application of CGP to prevent or control symptoms associated with the respiratory system, the subject has also used CGP to relieve symptoms during an episode of a condition of airway/upper respiratory tract. In one morning, during early product trials, after the subject discontinued use of CGP for about 24 hours, the subject appeared to exhibit the following symptoms associated with airway/upper respiratory tract: nasal congestion, throat irritation with post-nasal drip, hoarseness, and throat clearing, faint breathing sounds, and slightly short of breath. Although the symptoms did not amount to an asthma attack, the subject experienced significant discomfort. At about 10:45 A.M., the subject applied a double-dose of NasoCell (1.75% CGP by weight) via nasal inhalation in each nostril. At about 11:30 AM, the subject's symptoms were much improved. The subject then self-administered another dose of NasoCell in each nostril. At about 12:50 P.M., it appeared that the subject's symptoms had almost completely resolved. The subject had no trouble breathing while he was eating during lunch. At about 2:30 PM, the subject's symptoms were completely resolved. The subject's throat was cleared of any obstructions and breathing sounds, and was wide open. The subject's nasal passages were reopened and voice cleared from an earlier morning huskiness, characteristic of a post nasal drip condition. It is noteworthy that this subject observed that after some weeks of usage, much reduced usage was required to "maintain", and that this included the skipping of usage altogether, some days.

EXAMPLE 4

Applications of Calcium Glycerophosphate to a Human Subject Having Asthma

This Example describes a study of the effectiveness of calcium glycerophosphate to treat or prevent asthma in a human subject. A CGP composition similar to that described in Example 3, containing about 2% (w/w) CGP, was used in this study. A second human subject, a man of 44 years of age having a life history of asthma, participated in this study.

The subject intentionally stopped using Advair Diskus (steroid) for about 2 weeks. His allergies to molds were triggered by a 'musty' indoor environment resulting from several rainy and humid days. The allergies in turn triggered his asthma. The subject had felt a slight reduction in his airflow capacity for a few days, but had withheld use of albuterol inhaler (asthma rescue medication) during the day and only used it for severe wake-ups during the night. The subject had to use albuterol inhaler for three contiguous nights prior to the night described below.

In that night, at about 8:30 PM, the subject was experiencing difficulty breathing and wheezing, which signaled the start of an asthma attack. At about 8:35 PM, the subject applied two sprays of the CGP composition into each nostril and one spray of the CGP composition into his mouth for inhalation. An average spray delivery contained about 200 mg of the composition. At about 8:40 PM, the subject repeated the oral inhalation once, and the subject experienced mild relief to the extent that he did not feel the urgent need to use the albuterol inhaler. At about 8:52 PM, the subject did two additional oral inhalations of the composition. At about 8:55 PM, the subject noticed that his wheeze and tightness in chest were relieved about 80% or more. All nasal drips had been sniffed back in. At about 8:58 PM, the subject perceived a gradual improvement and experienced no labor in breathing. At about 9:05 PM, the subject felt better, but desired full relief and wanted to increase breathing capacity. He applied one inhalation of the composition into each nostril; paused to get full breath, then applied two deep oral inhalations of the composition at about 9:07 PM. At about 9:27 PM, the subject felt fine and substantially back to normal. At about 9:37 PM, the subject felt improved. At about 10:16 PM, the subject felt fully (100%) recovered. At about 11:00 PM, the subject felt fine, no worry, and went to bed. The subject experienced no wake-up with shortness of breath and did not use inhaler during the night. At about 8:00 AM the next day, the subject felt a little tightness in chest. Instead of using 2 puffs of albuterol to start the day as he normally did, the subject used the CGP composition. He applied two sprays of the composition into each nostril and two sprays of the composition into his mouth for inhalation. He felt relief and no need to use the albuterol inhaler.

EXAMPLE 5

Effectiveness of Calcium Glycerophosphate in Allergic Rhinitis Animal Models

This Example describes a study to determine whether repeated inhalation and intranasal instillation of calcium glycerophosphate attenuates ragweed induced nasal congestion and has an effect on nasal inflammation.

This study complied with all applicable sections of the Final Rules of the Animal Welfare Act regulations (9 CFR Parts 1, 2, and 3) and the *Guide for the Care and Use of Laboratory Animals* (National Research Council, 1996) with a study protocol reviewed and approved by the Institutional Animal Care and Use Committee (IACUC) before the initiation of the study. This study was conducted in the spirit of U.S. FDA 21 CFR Part 58 (Good Laboratory Practice for Nonclinical Laboratory Studies), even though not all study aspects were within strict compliance.

Beagle dogs immunized with ragweed (RW) as puppies develop allergic immune responses. These allergic dogs show elevated total and specific serum IgE and increased numbers of eosinophils in their blood and lungs, as well as an increase in airway resistance and a decrease in dynamic compliance after a challenge with RW by inhalation or local instillation in defined lung lobes. Additionally, these dogs develop increased nasal congestion and inflammation following RW challenge in the nose.

Ragweed sensitized beagle dogs (n=5) with preexisting nasal and airway allergic responses were utilized in the animal study described in this Example. Dogs served as their own control and initially were treated with vehicle (sterile water) and then rested for 5 weeks prior to receiving the test compound. The target dose of calcium glycerophosphate was about 30 mg/dog twice daily. The maximum concentration of the compound used for inhalation and nasal instillation was 20 mg/ml due to solubility issues. Based on the aerosol testing only 1.6 mg/dog could be delivered by inhalation during a 15 minute exposure (20 mg/ml solution). In addition, each dog received twice daily an intranasal instillation of 30 mg (2×375 μl of 20 mg/ml in each nostril) given within 30 minutes after the end of the inhalation exposures.

FIG. 1 summarizes the study design for characterizing the effects of CGP on rhinitis symptoms in ragweed sensitized Beagle dogs. The baseline nasal cavity volume was first measured 3 days (day −3) before each of the vehicle and CGP treatments. The dogs were treated with vehicle or CGP (day 0) twice daily with the target dosage described above. Three days into the vehicle or CGP treatment, nasal challenge with ragweed was performed (day 3). Treatment with vehicle or CGP continued during the assessment of rhinitis endpoints, e.g., total treatment duration=6 days (day 0-5) for each of the vehicle and CGP treatments. There were 5 weeks following the first intranasal RW challenge during the vehicle treatment and the CGP treatment.

Vehicle (sterile water) was given twice daily by inhalation (15 minutes) followed by intranasal instillation of water (2×250 μl in each nostril). The test compound calcium glycerophosphate was formulated in sterile water at a dose of 20 mg/ml and given by inhalation (deposition 1.6 mg). The test-article and the compound solution were prepared in the morning of each treatment day. Vehicle and test-article were administered by inhalation and intranasal instillation twice a day. Dosing of vehicle or test compound was achieved by utilizing a face mask connected to a jet nebulizer for inhalation delivery followed by intranasal instillation in both nostrils using an Accuspray device.

Treatment occurred on Days 0 to 5 (only AM on Day 5). Vehicle and compound were delivered in the morning (8:15-9:10 am) and the afternoon (2:00-3:30 pm). On days when acoustic rhinometry procedures were performed (Days 0), the morning dosing occurred such that the procedures were performed within 1-6 h after dosing. The pH of the compound (as administered for nasal inhalation) was recorded prior to administration. As identified in the aerosol exposure the average pH of the nebulizer solution was 8.85.

Blood sample was collected by placing a venous (cephalic or saphenous) catheter in the leg prior to anesthesia or by venipuncture (jugular) using a syringe or needle-vacutainer. On the study Days −3 (baseline), 3, and 5 two to 3 ml blood samples were collected for vehicle and compound experiment prior to exposures and intranasal instillation for chemistry and CBC analysis.

Rhinitis assessments were conducted using one or more of the following tests.

Nasal cavity geometry (AcR) pre/post antigen challenge in both nares
  1. time 0 (just prior to RW instillation)
  2. at 15, 30, 45, 60, 75, 90 min, 24 h and 48 h post RW challenge Nasal lavage of both nares at baseline and at 24 h (Day 4) and 48 h (Day 5) post RW instillation and only one side at 15, 30, 45 and 60 min post RW challenge (Day 3)
  1. Release of histamine, leukotrienes and prostaglandins in nasal lavage fluid baseline (prior to compound or RW treatment/challenge), 15, 30, 45, 60 min and 24 h post RW instillation
  2. Nasal lavage cells from the baseline (Day−3), 24 h (Day 4) and 48 h (Day 5) hour lavage were used for determination of inflammatory cell differentials
  3. Excess nasal lavage fluid was frozen for analysis of cytokines.

Cardiovascular readouts (heart rate, O2 saturation, body temperature) throughout nasal congestion measurement.

Measurement of Nasal Cavity Geometry by Acoustic Rhinometry—Rhinitis Assessment

Acoustic rhinometery was measured on experimental Days 3, 4, and 5. Nasal cavity volume was measured in anesthetized dogs using an Eccovision Acoustic Rhinometry System (Hood Laboratories, Inc., Pembroke, Mass.). Briefly, a wave tube containing a spark sound generator was connected with the nasal cavity using a plastic nose piece. Based on nasal cast impressions and X-ray measurements from the dog nasal cavity, a distance from the nostril opening into the nasal cavity of 10 cm was used for all experiments. Acoustic reflections were converted to area-distance function curves and used to determine nasal cavity volume. Heart rate and $O_2$ saturation were measured throughout the experiment. Body temperature was checked occasionally. To avoid a rapid drop in body temperature associated with general anesthesia dogs were placed on a water circulating heating pad during the experiment if necessary. Nasal cavity volume was measured before and at different time points after nasal RW challenge (both nares; 0, 15, 30, 45, 60, 75, and 90 minutes, 24 h, 48 h post RW challenge). Nasal lavages were performed at specific time points before and after RW challenge in both nares at baseline (Day −3), and at 24 (Day 4) and 48 h (Day 5) post RW challenge and only one side at 15, 30, 45, and 60 min post challenge (Day 3).

Anesthesia—Rhinitis Assessment

Dogs were anesthetized with isoflurane (5% induction; 1 to 1.5% maintenance). Briefly, custom made face masks constructed out of rubber material were placed over the muzzles of the dogs for the induction of anesthesia to avoid isoflurane entering the nasal passages. The face masks had a hole cut in the end to allow a brass tubing to protrude out approximately 1 to 2 cm while sealing around its outside. The face masks also occluded the nares of the dogs, thus, assuring mouth-only inhalation of the anesthetic. After inducing anesthesia, an endotracheal tube was placed in the trachea and anesthesia was maintained with isoflurane throughout the experiment. Dogs were placed in a supine position for the nasal congestion measurements and in a prone position with a slightly tilted head for the nasal lavage procedure.

Nasal Ragweed Challenge by Instillation

Ragweed extract (RW short, Ambrosia artemisifolia, Greer, Lenoir, N.C.; 6 mg/ml in 0.25 ml PBS) was instilled in both nares using an Accuspray device (Becton Dickinson).

Nasal Lavage

While under anesthesia a flexible plastic catheter was inserted several centimeters into the dog's nare. The nare was washed with a phosphate buffered saline solution (PBS; 3×5 ml for collection of cells [baseline, 24 and 48 h post RW challenge]; 1×5 ml for collection of fluid for mediators [15, 30, 45, and 60 minutes post RW challenge]).

Pathologic Analyses

Total nasal cells were determined using an automatic cell counter. Cells were spun onto slides by cytocentrifugation and stained with a modified Wright-Giemsa stain. At least four hundred inflammatory cells (or less if applicable) were counted and the percentage of specific cell types determined for each animal (slides in duplicates, 200 cells per slide). The first lavage fluid sample (after centrifugation) was frozen separately for mediator analysis. Mediator analysis for histamine, leukotrienes, and prostaglandins were performed according to the kit manufacturer instructions (Immunotech—Beckman Coulter Company #IM2015, Neogen Corporation #406410, Cayman Chemical Company: PGE2—#514010, PGD2—#512011, respectively).

Daily Observations

Animals were examined twice per day (morning and afternoon) on each day of the study. Examination was oriented toward identifying the onset and progression of any abnormal clinical signs. No adverse health effects were found during the duration of the experiments.

Body Weights

All animals were weighed on study Days −3, 3 and 5 only for compound experiment (Table 1).

TABLE 1

Body weight (kg) for all dogs during vehicle and compound treatment.

| | Vehicle | | | Calcium Glycerophosphate | | |
|---|---|---|---|---|---|---|
| Animal | Day −3 | Day 3 | Day 5 | Day −3 | Day 3 | Day 5 |
| 1 | 10.5 | 10.8 | NA | 10.8 | 10.4 | 10.4 |
| 2 | 10.25 | 10.0 | NA | 10.7 | 10.6 | 10.55 |
| 3 | 12.5 | 12.7 | NA | 13.0 | 13.3 | 13.2 |
| 4 | 10.5 | 10.3 | NA | 10.4 | 10.3 | 10.4 |
| 5 | 10.0 | 9.9 | NA | 9.8 | 9.9 | 9.8 |

Statistical Analysis

Changes in nasal cavity volume or mediator levels were assessed by two way analysis of variance (ANOVA) with Bonferroni post-test. All other statistical comparisons were made using ANOVA with Dunnett's multiple comparison test or paired two tailed t-test if appropriate. A value of $p<0.05$ was considered statistically significant.

Other parameters were also measured from the dogs at various time points and compared between the treatments with vehicle and CGP.

A total of 5 ragweed-sensitized dogs were used in this experiment. All dogs received vehicle first and after a 5 week recovery period, they were treated with calcium glycerophosphate by inhalation followed by intranasal instillation. Due to solubility of the compound only about 1.6 mg were deposited in the lung by inhalation and a total of 30 mg were intranasally instilled using a BD accuspray device twice a day for a total of 5 days.

Figure 3:
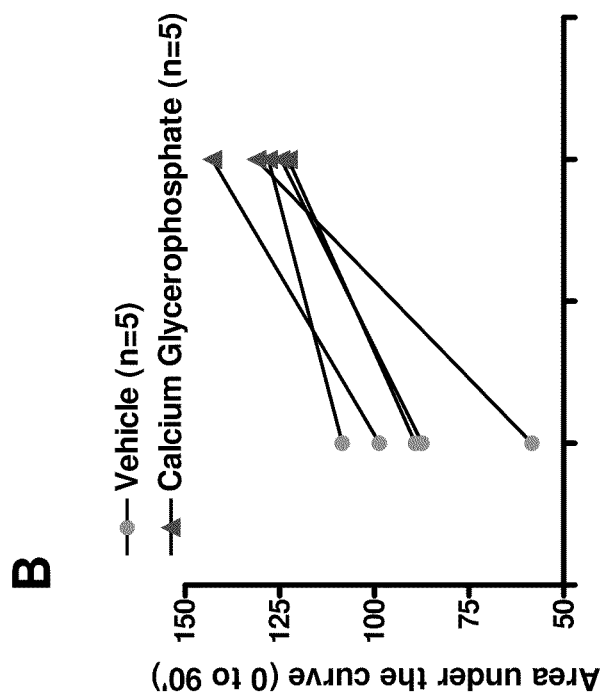
FIG. 3 shows the area under the curve (AUC) of the change in nasal cavity volume between 0 and 90 min as shown in FIG. 2 expressed as mean±sem (A, n=5) and as scatter graph for individual dogs (B), the AUC was significantly increased after CGP treatment compared to vehicle control determined by Paired t-test (p=0.0092) indicating an attenuation of the nasal congestion induced by ragweed instillation.
Figure 3:
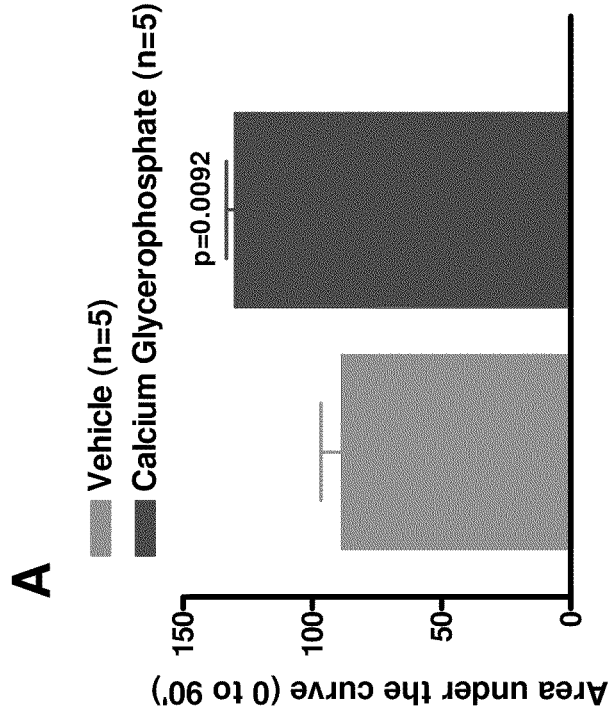
Figure 4:
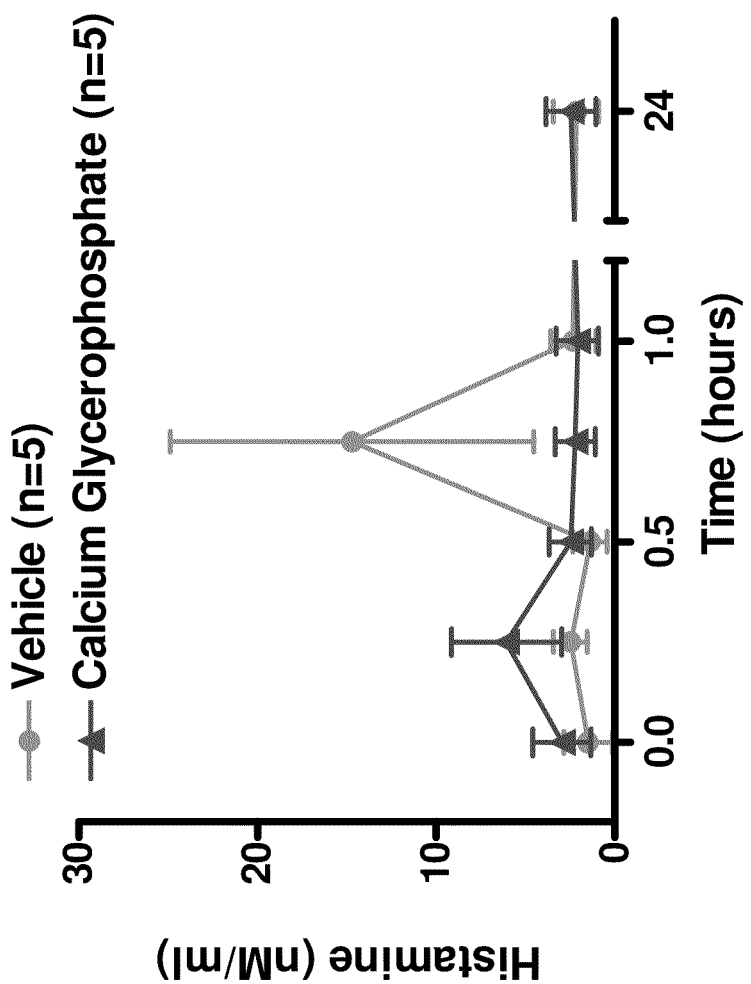
FIG. 4 shows histamine levels in nasal lavage fluid measured before and after intranasal ragweed challenge done three days after first treatment with vehicle or compound: data are expressed as mean±sem (n=5); $T_0$ indicates baseline sample collected the day before the initiation of either vehicle or calcium glycerophosphate treatment; dogs served as their own control and vehicle treatment was compared to compound treatment; no statistical significance was reached by an analysis under One Way Anova followed by Dunnett's post-test.
Figure 5:
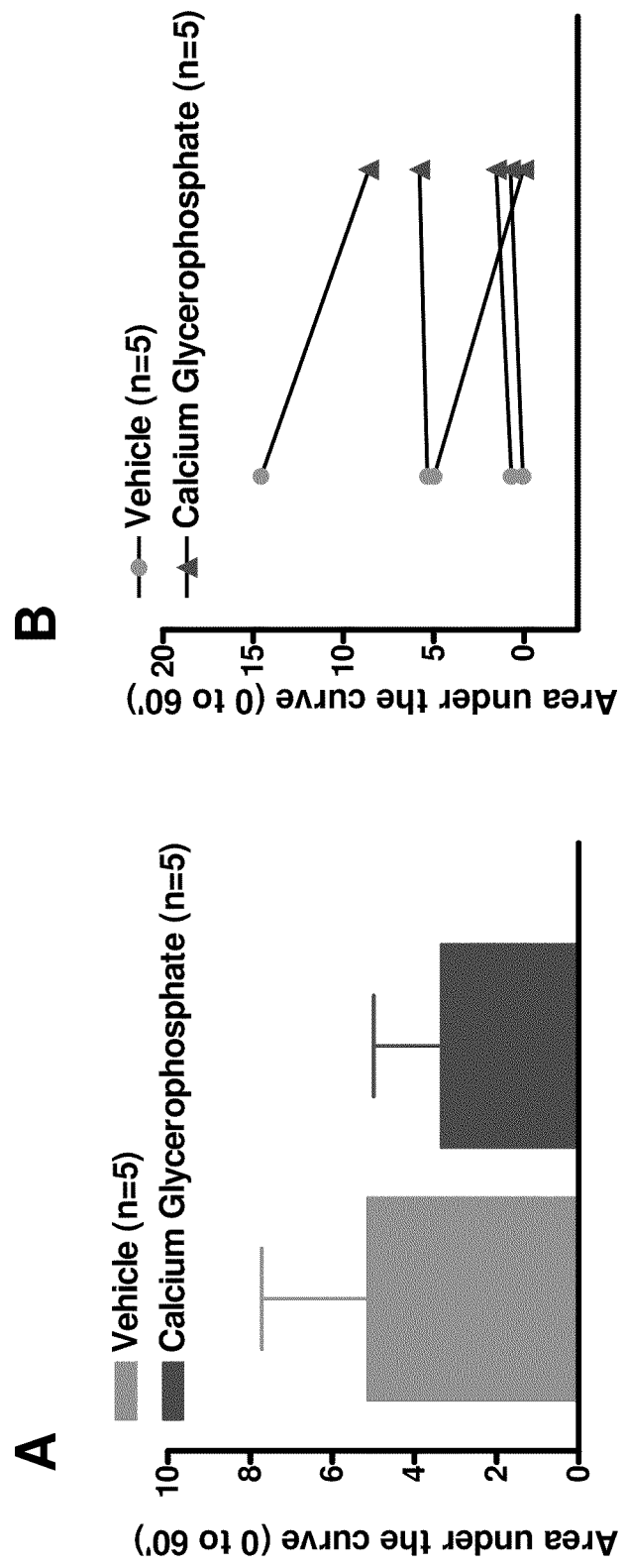
FIG. 5 shows the AUC calculated for the histamine levels between 0 and 60 min in FIG. 4 for vehicle and compound treatment expressed as mean±sem (A, n=5) and individual data points in a scatter graph (B); histamine levels decreased in two of the 5 dogs, no statistical significance was reached.
Figure 6:
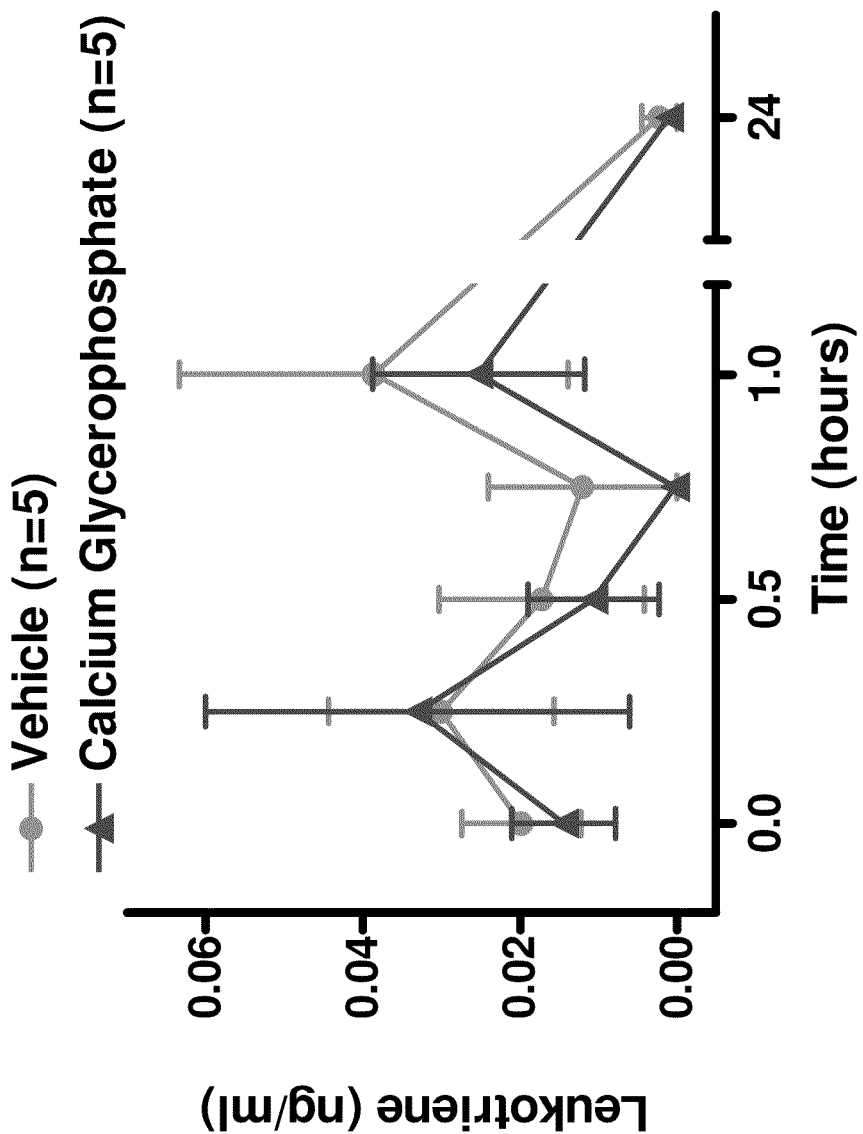
FIG. 6 shows levels of leukotriene $C_4/D_4/E_4$ in nasal lavage fluid measured before and after intranasal ragweed challenge done three days after first treatment with vehicle or compound; data are expressed as mean±sem (n=5); $T_0$ indicates baseline sample collected the day before the initiation of either vehicle or calcium glycerophosphate treatment; dogs served as their own control and vehicle treatment was compared to compound treatment; no statistical significance was reached by an analysis under One Way Anova followed by Dunnett's posttest.
Figure 7:
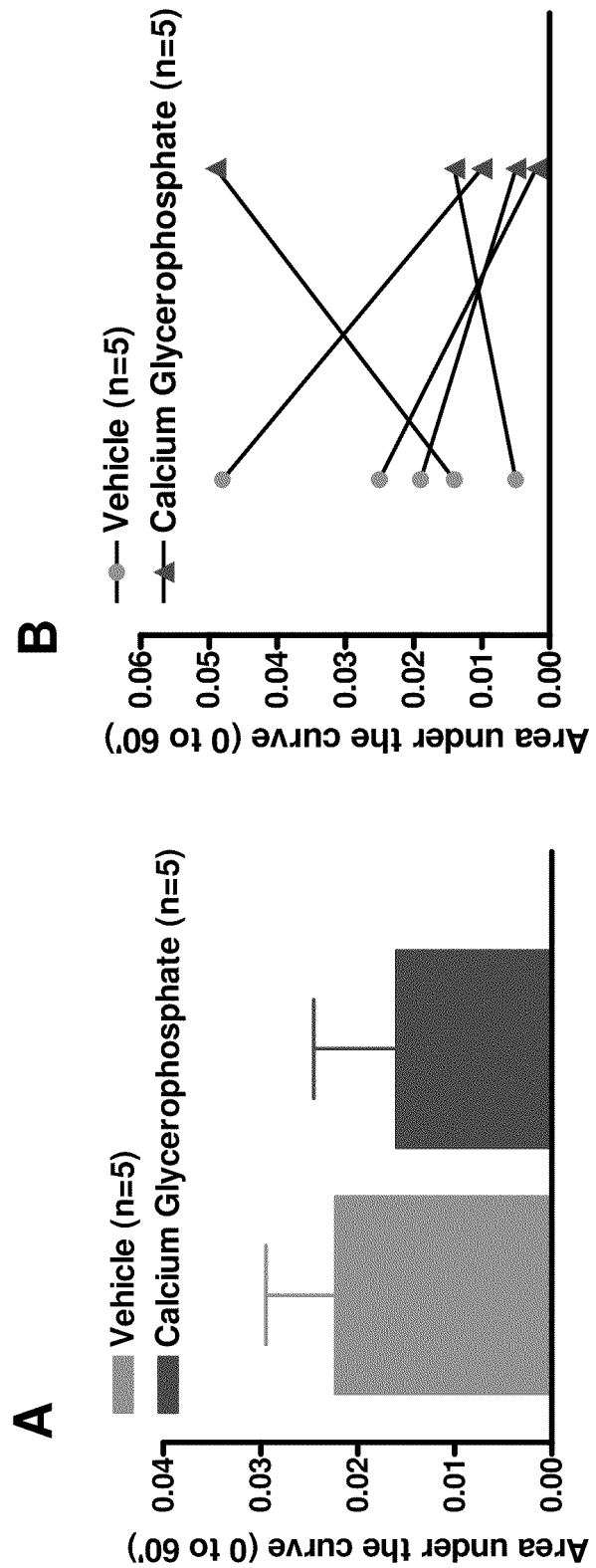
FIG. 7 shows the AUC calculated for the levels of leukotriene $C_4/D_4/E_4$ between 0 and 60 min in FIG. 6 for vehicle and compound treatment shown as mean±sem (A, n=5) and individual data points in a scatter graph (B); leukotriene levels decreased in three dogs and increased in two dogs and no statistical significance was reached.
Figure 8:
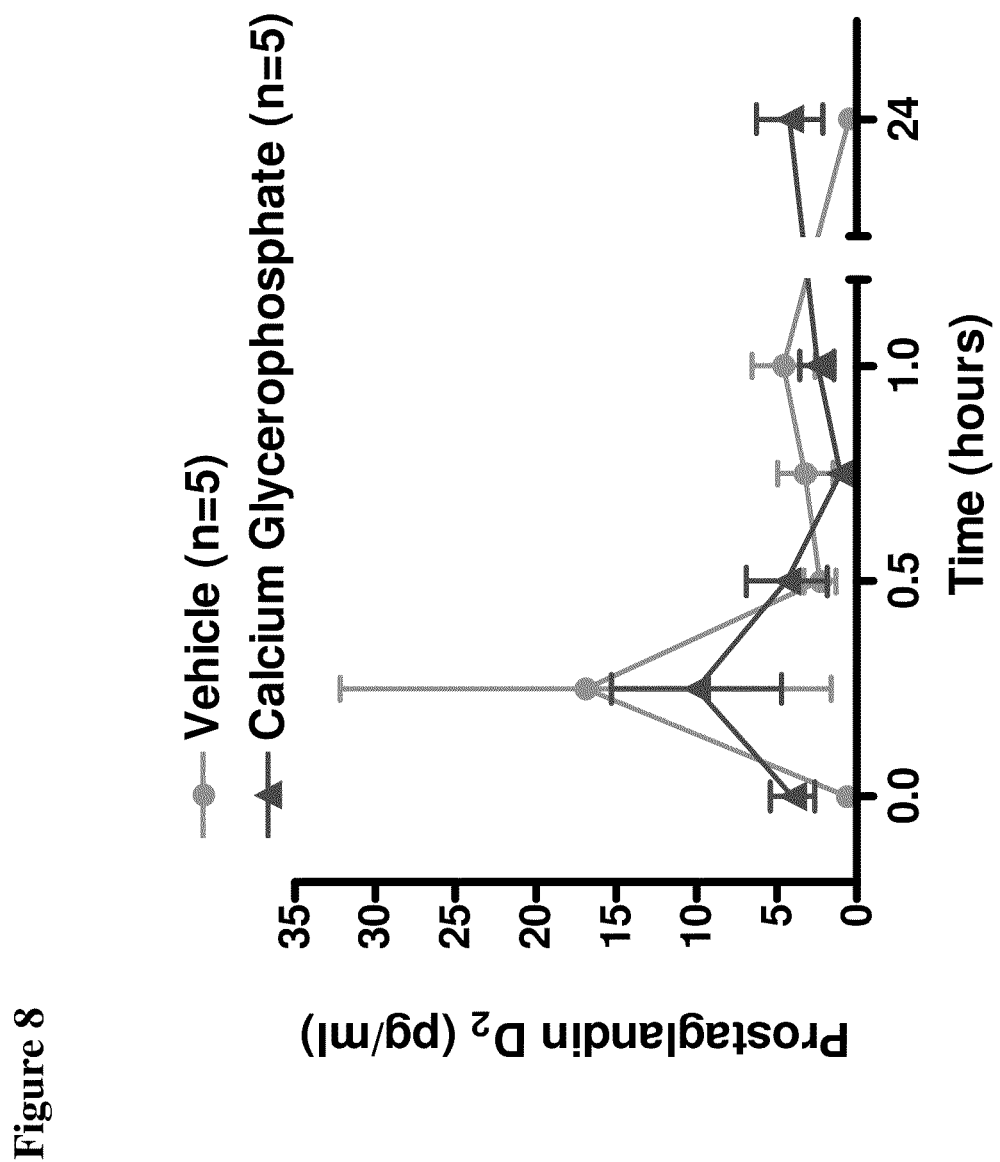
FIG. 8 shows prostaglandin $D_2$ levels in nasal lavage fluid measured before and after intranasal ragweed challenge done three days after first treatment with vehicle or compound; data are expressed as mean±sem (n=5); $T_0$ indicates baseline sample collected the day before the initiation of either vehicle or calcium glycerophosphate treatment; dogs served as their own control and vehicle treatment was compared to compound treatment; no statistical significance was reached by an analysis under One Way Anova followed by Dunnett's posttest.
Figure 9:
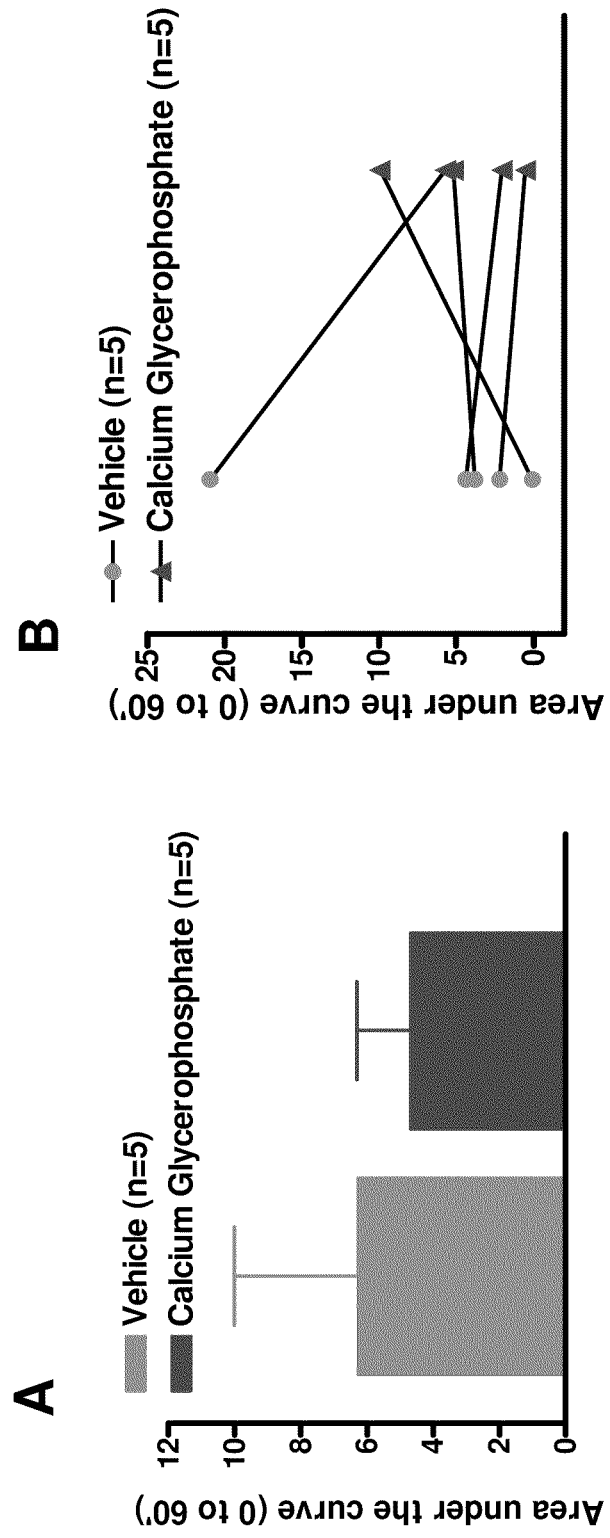
FIG. 9 shows the AUC calculated for the prostaglandin $D_2$ levels between 0 and 60 min in FIG. 8 for vehicle and compound treatment shown as mean±sem (A, n=5) and individual data points in a scatter graph (B); prostaglandin $D_2$ levels decreased in three dogs and increased in two dogs and no statistical significance was reached.

The results for all variables (change in nasal cavity volume and mediators in nasal lavage fluid) are shown over time as a comparison between treatment group and vehicle before and up to 24 or 48 hours after treatment. The area under the curve (AUC) for the change in nasal cavity volume from baseline (0 to 90 minutes post ragweed) and the AUC for the change in mediator levels over time (0 to 60 minutes post ragweed) were calculated for each treatment. An increase in AUC for compound treatment compared to vehicle indicates an increase in nasal cavity volume and therefore a decrease in nasal congestion (FIG. 3). In contrast, a decrease in AUC for the mediator levels (e.g. histamine, leukotrienes, prostaglandins) indicates an attenuation of these mediators due to compound treatment (FIGS. 5, 7 and 9). An area under the curve of 150 is the equivalent of a 100% increase in nasal cavity volume and no change in AUC (same as vehicle) indicates no change in nasal cavity volume (=0%). The AUC is always shown as an average including standard error for each treatment group and as changes for each individual dog between vehicle and compound treatment.

Figure 2:
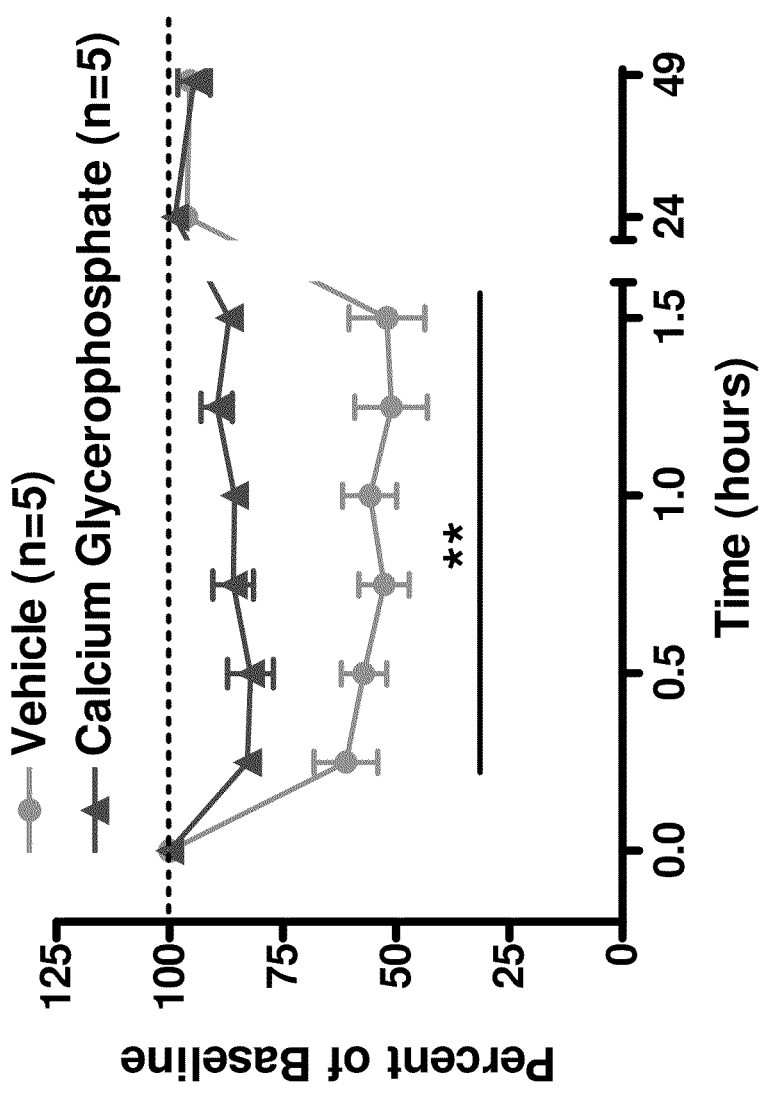
FIG. 2 illustrates percentage of nasal cavity volume relative to that of baseline (time 0) measured before and after intranasal ragweed challenge: nasal congestion was measured three days after first inhalation and IN treatment with vehicle or CGP (1.5 mg inhale+30 mg IN); dogs served as their own control and vehicle experiment was performed about 5 weeks prior to compound treatment; data are expressed as mean±sem (n=5); nasal congestion was significantly attenuated compared to vehicle treatment determined by Two Way Anova (p=<0.0001) followed by Bonferroni posttest at individual time points (** p<0.01)

As shown in FIGS. 2 and 3, repeated treatment (BID) with calcium glycerophosphate by inhalation (1.6 mg deposition) and intranasal instillation (30 mg) starting three days prior to nasal ragweed challenge significantly increased nasal cavity volume and therefore attenuated nasal congestion compared to vehicle treatment (Two Way Anova, $p<0.0001$). The attenuation was statistically significant at all time points from 15 to 90 minutes post ragweed ($p<0.05$, Bonferroni posttest).

It has been shown previously that treatment with a-adrenergic agonist, pseudoephederine (PSE; 3 mg/kg) and histamine H1 antagonist, chlorpheniramine (10 mg/kg), in the same manner as that in the present study can prevent the development of RW-induced nasal congestion (Rudolph et al., 2003, *Am J Rhinol.*, 17(4):227-32). The response of calcium glycerophosphate is similar to that observed previously with PSE and chlorpheneramine with respect to the attenuation of nasal congestion induced by intranasal ragweed challenge.

The histamine, leukotriene and prostaglandin $D_2$ and $E_2$ levels in nasal lavage fluid were partially altered after treatment with the compound compared to vehicle treatment. In general, the levels of histamine, leukotriene and prostaglandin $D_2$ in nasal lavage fluid increased over time compared to baseline levels after vehicle treatment. Statistical significance was not reached between vehicle and compound treatment by an analysis under One Way Anova followed by Dunnett's posttest.

The variable effects of compound treatment on individual dogs, e.g., with some dogs showing a negligible effect and others showing a more dramatic effect, have also been observed with other compounds. In general, the dogs' response to RW challenge remains consistent following repeated RW challenges, and decreases in nasal congestion are due to compound treatment, not due to variability in the response over time. A high degree of variability in the peak levels of mediators, e.g., leukotrienes, prostaglandins, and histamine, has also been generally observed following RW challenge. In addition, other compounds that have resulted in reduced nasal congestion have also been associated with or without significant reductions in the mediators.

Figure 10:
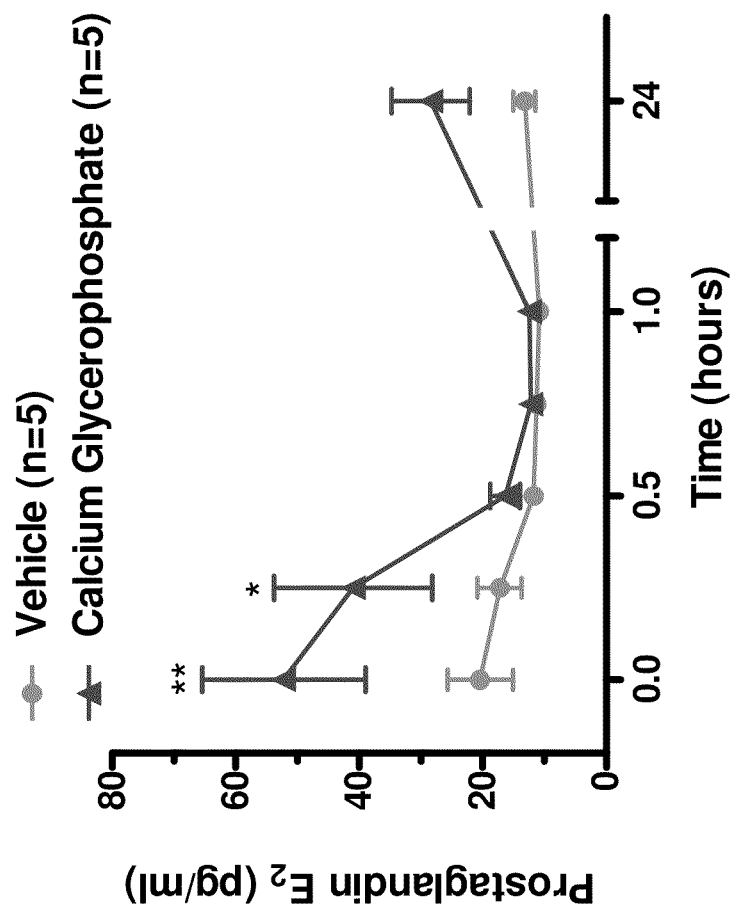
FIG. 10 shows prostaglandin $E_2$ levels in nasal lavage fluid measured before and after intranasal ragweed challenge done three days after first treatment with vehicle or compound; data are expressed as mean±sem (n=5); $T_0$ indicates baseline sample collected the day before the initiation of either vehicle or calcium glycerophosphate treatment; dogs served as their own control and vehicle treatment was compared to compound treatment; no statistical significance was reached by an analysis under One Way Anova followed by Dunnett's posttest.
Figure 11:
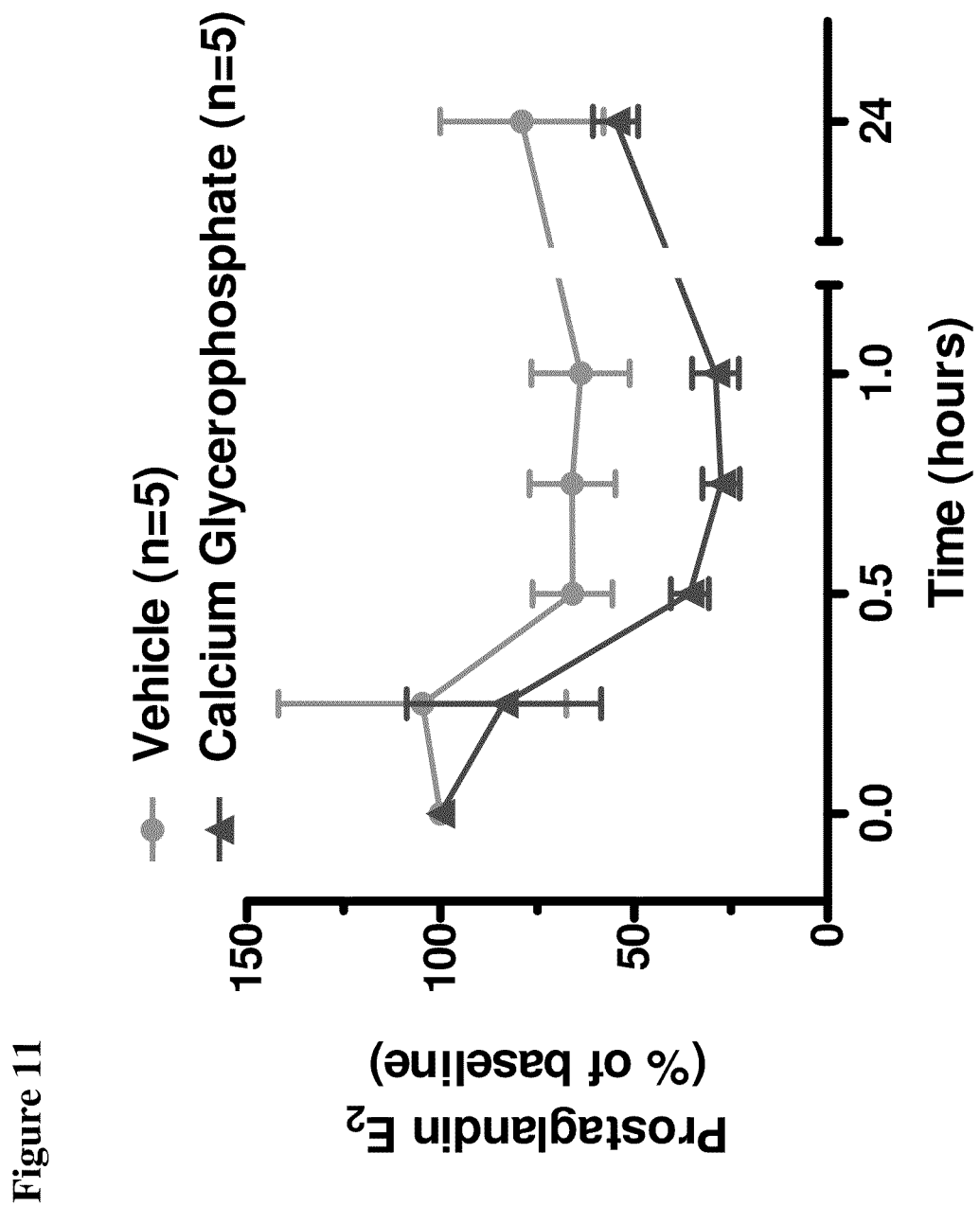
FIG. 11 shows that after the data in FIG. 10 were normalized to take into account of the differences in the initial baseline levels ($T_0$) of prostaglandin $E_2$ prior to treatment (e.g. baseline=100%), prostaglandin $E_2$ levels were significantly attenuated compared to vehicle treatment determined by Two Way Anova (p=<0.009) followed by Bonferroni posttest at individual time points (no significance at individual time points)

Interestingly, $PGE_2$ levels were elevated in the dogs prior to the initiation of the calcium glycerophosphate treatment leg (e.g. $T_0$ [baseline] levels). Levels of $PGE_2$ decreased following ragweed challenge during the calcium glycerophosphate treatment (FIG. 10). Upon RW challenge the $PGE_2$ levels returned (T30-60 min) to levels measured following the vehicle treatment leg and then were elevated at 24 h post RW challenge. This decrease in changes in PGE2 levels, with the graphs normalized for both treated and untreated groups' baselines, achieves statistical significance in favor of the treated group. $PGE_2$ has both inflammatory and anti-inflammatory properties. $PGE_2$ promotes vasodilation by activating cAMP-coupled EP2 receptors on vascular smooth muscle and increases vascular permeability indirectly by enhancing the release of histamine and other mediators from tissue leukocytes such as mast cells. As inflammation progresses, $PGE_2$ synthesis by macrophages is enhanced due to increased expression of COX-2 and PGE-synthase. $PGE_2$ inhibits leukocyte activation and promotes bronchodilation through activation of $G_s$-coupled EP2 and EP4 receptors (Tilley et al., 2001, *J Clin invest*. 108(1): 15-23). The elevated levels prior to calcium glycerophosphate may be the result of the initial RW challenge during the vehicle leg, despite the 5 weeks of rest in between. When PGE2 levels are normalized to baseline levels, there was an overall effect of treatment with calcium glycerophosphate, e.g. a greater reduction in PGE2 levels following RW challenge in conjunction with calcium glycerophosphate treatment, even though there was no significant effect at any specific time point (Two-way ANOVA with Bonferroni post test; FIG. 11). The overall greater reduction of $PGE_2$ following RW challenge in conjunction with calcium glycerophosphate treatment suggests that $PGE_2$ may be a potential underlying mechanism for the effects of calcium glycerophosphate.

Figure 12:
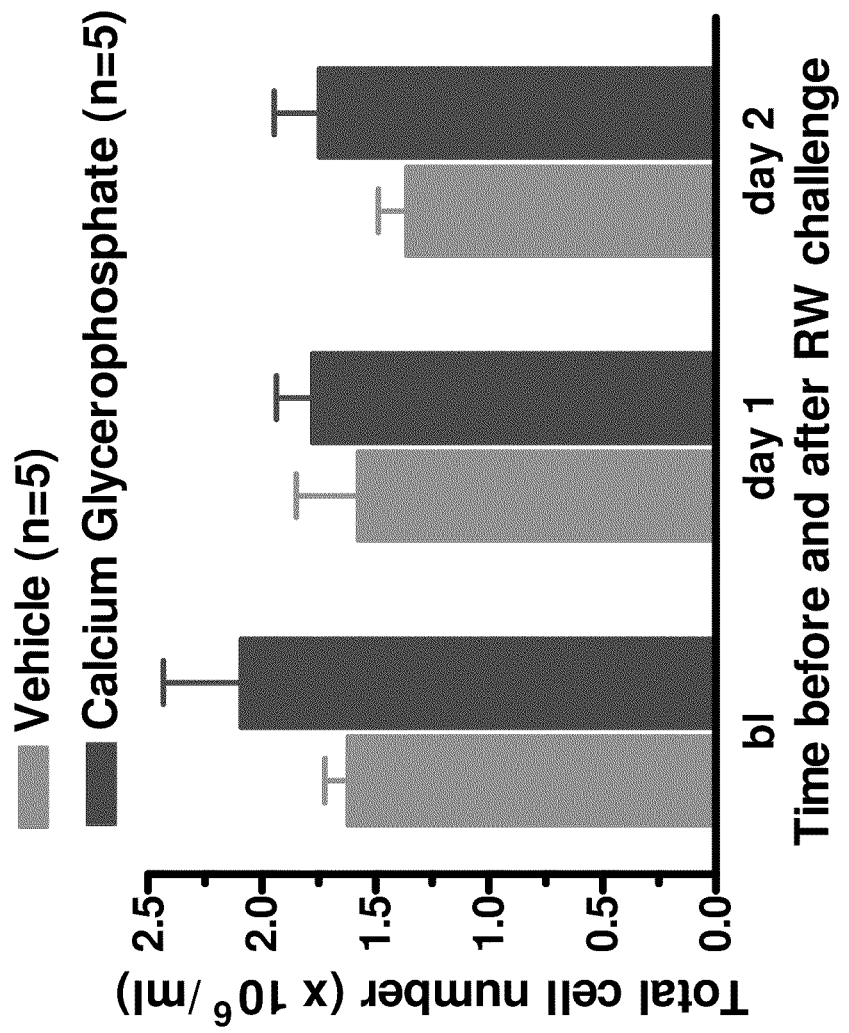
FIG. 12 shows the total numbers of cells in nasal lavage (including epithelial cells) collected before and after repeated oral treatment with vehicle and calcium glycerophosphate; nasal lavages were performed prior to first treatment and on Days 1 and 2 after nasal RW challenge on $4^{th}$ day of treatment.
Figure 13:
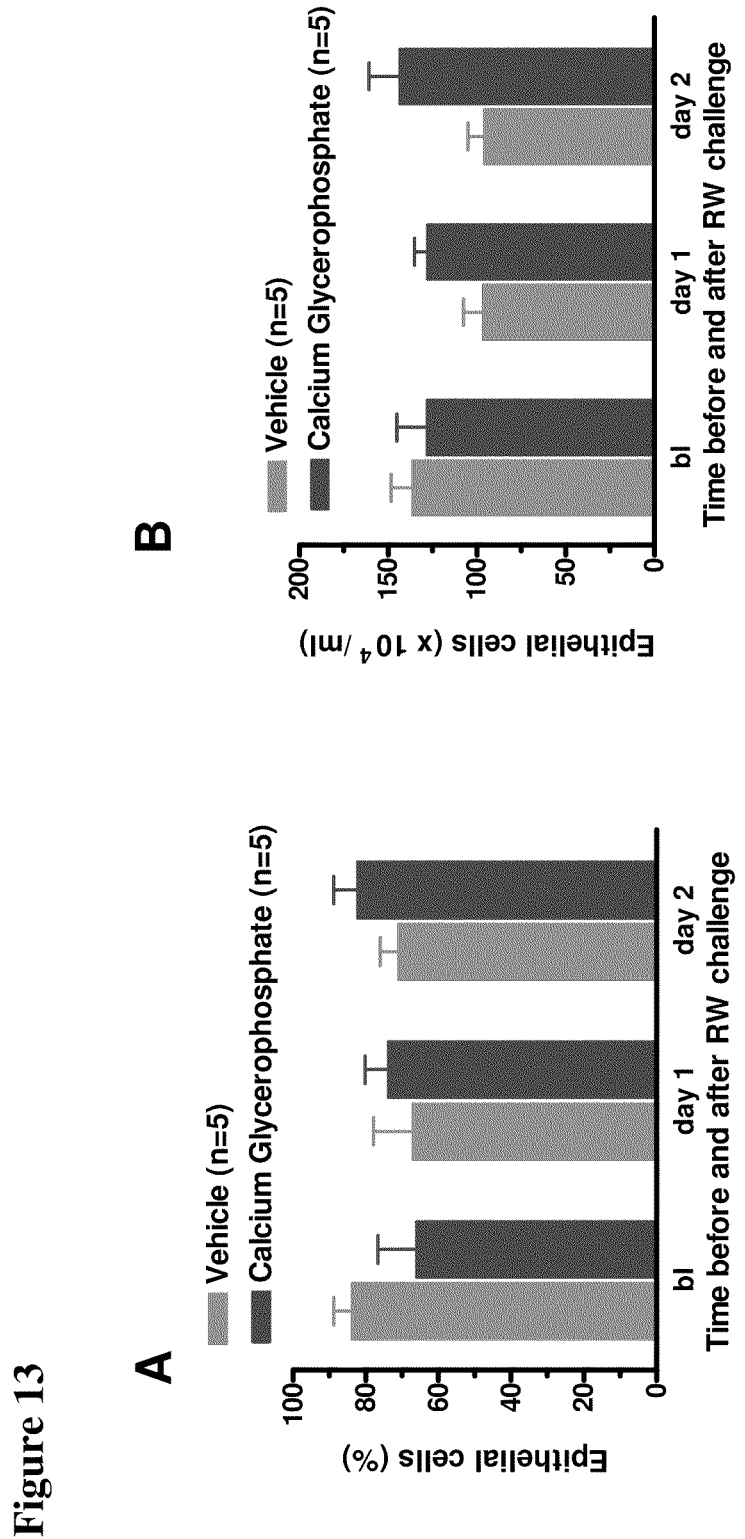
FIG. 13 shows epithelial cells in nasal lavage expressed as percentage of total cells (A) and as number of cells (B) collected before and after repeated oral treatment with vehicle and calcium glycerophosphate; nasal lavages were performed prior to first treatment and on Days 1 and 2 after nasal RW challenge on $4^{th}$ day of treatment.
Figure 14:
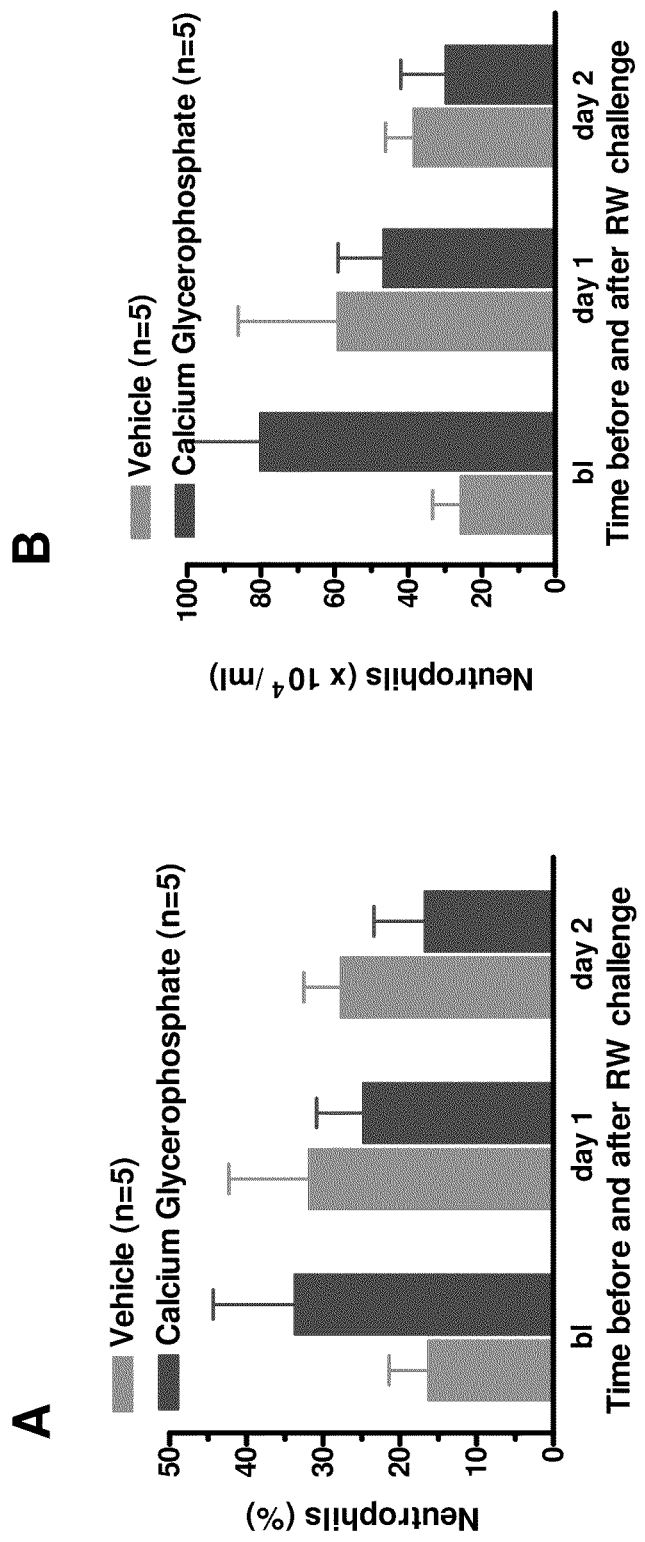
FIG. 14 shows neutrophils in nasal lavage expressed as percentage of total cells (A) and as number of cells (B) collected before and after repeated oral treatment with vehicle and calcium glycerophosphate; nasal lavages were performed prior to first treatment and on Days 1 and 2 after nasal RW challenge on $4^{th}$ day of treatment.
Figure 15:
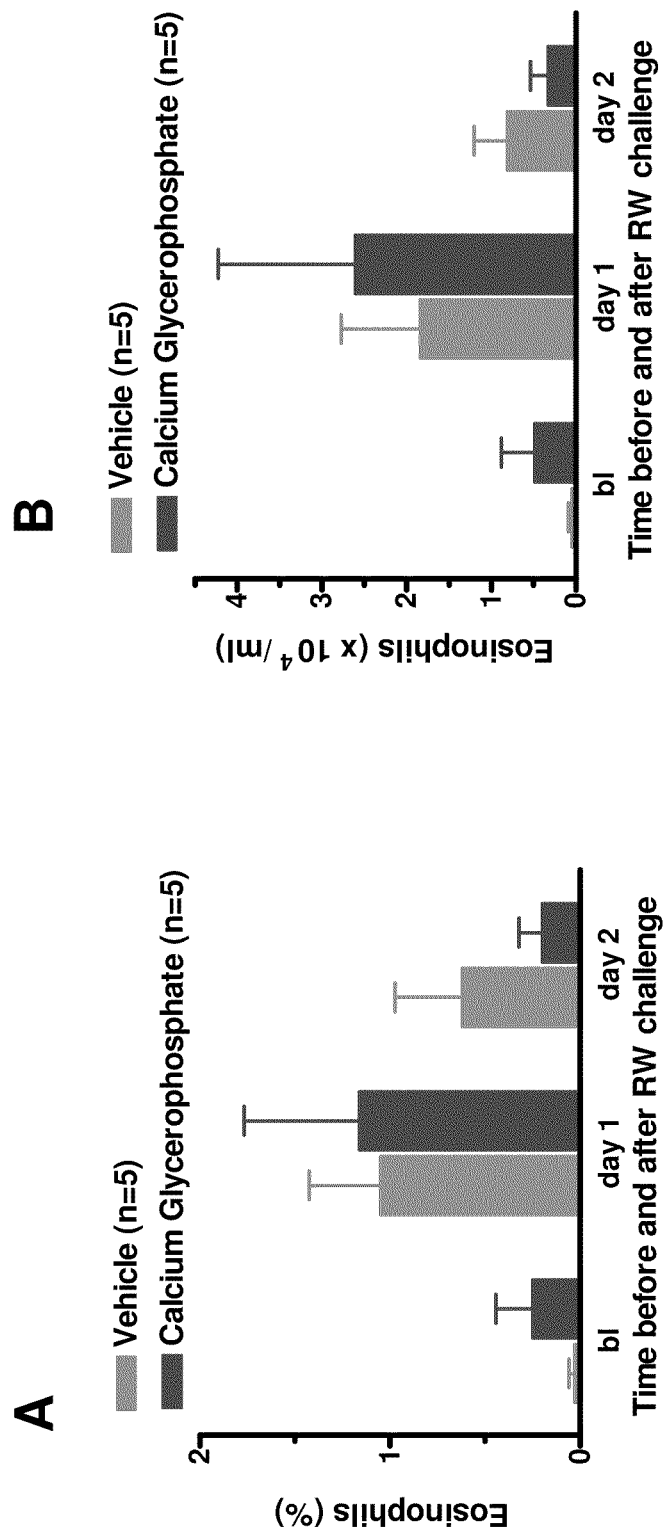
FIG. 15 shows eosinophils in nasal lavage expressed as percentage of total cells (A) and as number of cells (B) collected before and after repeated oral treatment with vehicle and calcium glycerophosphate; nasal lavages were performed prior to first treatment and on Days 1 and 2 after nasal RW challenge on $4^{th}$ day of treatment.
Figure 16:
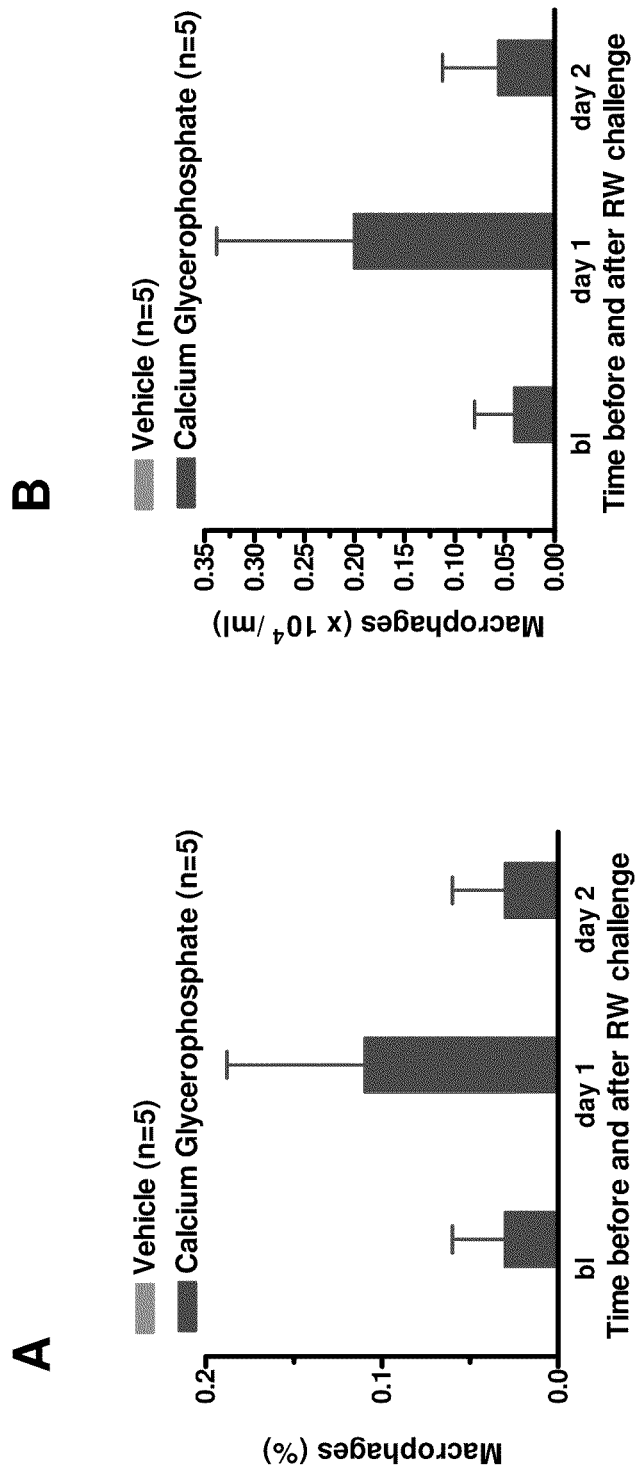
FIG. 16 shows macrophages in nasal lavage expressed as percentage of total cells (A) and as number of cells (B) collected before and after repeated oral treatment with vehicle and calcium glycerophosphate; nasal lavages were performed prior to first treatment and on Days 1 and 2 after nasal RW challenge on $4^{th}$ day of treatment.
Figure 17:
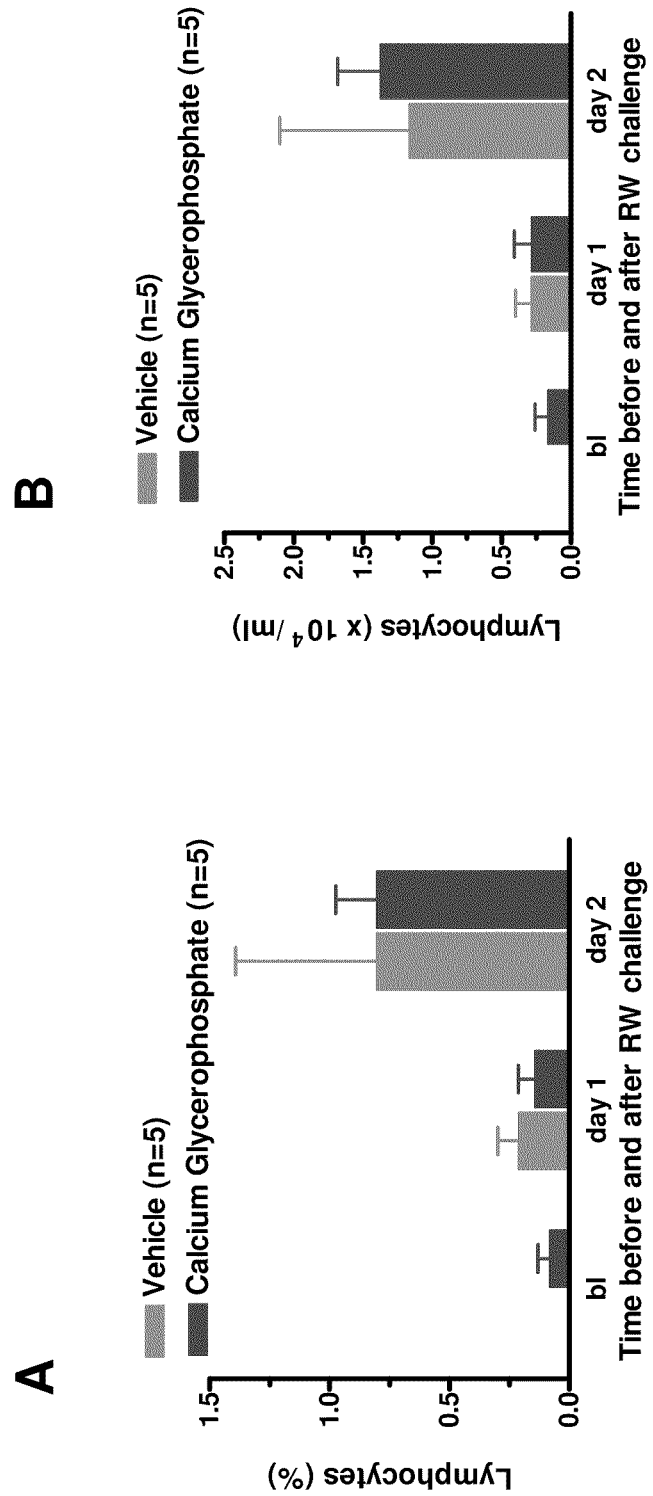
FIG. 17 shows lymphocytes in nasal lavage expressed as percentage of total cells (A) and as number of cells (B) collected before and after repeated oral treatment with vehicle and calcium glycerophosphate; nasal lavages were performed prior to first treatment and on Days 1 and 2 after nasal RW challenge on $4^{th}$ day of treatment.

The total collected cells include inflammatory cells and epithelial cells (FIG. 12). Epithelial cells and all inflammatory cells are shown as percentage of cells counted (FIGS. 13 to 17, panel A) and as number of cells based on total number of cells collected (FIGS. 13 to 17, panel B). In this study the assessment of the number of inflammatory cells in the nasal lavage showed that pretreatment with calcium glycerophosphate did tend to reduce the lung inflammatory cells compared to vehicle treatment, although none of the endpoints reached statistical significance under the current analysis. In general, RW challenge resulted in an increase in eosinophils on Day 1 and Day 2 post challenge. Levels of macrophages following vehicle treatment were not detectable and were at negligible levels following calcium glycerophosphate treatment.

Treatment with calcium glycerophosphate was well tolerated by the animals and no visible adverse clinical signs were observed or any significant effects on blood chemistry parameters.

Overall, the response seen following calcium glycerophosphate treatment is similar to the responses previously observed with an α-adrenergic agonist, pseudoephederine, a histamine H1 antagonist, chlorpheniramine, and montelukast in this model. Results of the animal study further demonstrate that CGP is effective to relive nasal congestion, thus useful for treating or preventing a disease, disorder and/or condition of a respiratory system related to an obstructive or a restrictive condition of the respiratory airway, such as rhinitis, asthma, and other Th2 inflammatory conditions.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating rhinitis, allergic asthma or a chronic obstructive pulmonary disease (COPD) in a subject in need thereof, the method comprising administering to the respiratory system of the subject an effective amount of calcium glycerophosphate, wherein the calcium glycerophosphate is orally administered to the respiratory system of the subject in a composition formulated for oral administration in a dosage of about 440 µg to about 88 mg of the, calcium glycerophosphate per administration.

2. The method of claim 1, wherein the calcium glycerophosphate is administered to the respiratory system of the subject by a spray, a quick-dissolving tablet, an oral inhalation solution or suspension, a syrup, a mechanized intermittent fluid pulser, an atomizer, a vaporizer, or an insufflator.

* * * * *